United States Patent [19]

Camble et al.

[11] Patent Number: 5,416,195

[45] Date of Patent: May 16, 1995

[54] POLYPEPTIDE DERIVATIVES OF GRANULOCYTE COLONY STIMULATING FACTOR

[75] Inventors: Roger Camble, Macclesfield; Heather Carr, Bollington; David Timms; Anthony J. Wilkinson, both of Macclesfield, all of England

[73] Assignee: Zeneca Limited, London, England

[21] Appl. No.: 692,995

[22] Filed: Apr. 29, 1991

[30] Foreign Application Priority Data

| Apr. 30, 1990 [GB] | United Kingdom | 9009623 |
| Jun. 20, 1990 [GB] | United Kingdom | 9013773 |
| Jul. 24, 1990 [GB] | United Kingdom | 9016215 |
| Feb. 11, 1991 [GB] | United Kingdom | 9102799 |

[51] Int. Cl.$^6$ ............................................. C07K 13/00
[52] U.S. Cl. ............................ 530/351; 530/395; 930/145; 424/85.1
[58] Field of Search ............ 530/351, 395; 930/145; 514/8; 424/85.1

[56] References Cited

U.S. PATENT DOCUMENTS

| 4,810,643 | 3/1989 | Souza | 436/172.3 |
| 5,104,651 | 4/1992 | Boone et al. | 530/351 |
| 5,214,132 | 5/1993 | Kuga et al. | 530/351 |
| 5,218,092 | 6/1993 | Sasaki | 530/351 |

FOREIGN PATENT DOCUMENTS

| 0243153 | 10/1987 | European Pat. Off. |
| 0272703 | 6/1988 | European Pat. Off. |
| 0289267 | 11/1988 | European Pat. Off. |
| 0347041 | 12/1989 | European Pat. Off. |
| 456200 | 11/1991 | European Pat. Off. |
| 8905824 | 6/1989 | WIPO |
| 9012874 | 1/1990 | WIPO |
| 9006952 | 6/1990 | WIPO |

OTHER PUBLICATIONS

Wingfield et al, Biochem J 256(1) 1988, pp. 213-218 (abst only).

Clark-Lewis et al, Structure-Function Studies of Human Granulocyte-Macrophage Colony-Stimulating Factor, The Journal of Immunology, vol. 141, 881-889, Aug. 1, 1988.

Primary Examiner—Garnette D. Draper
Assistant Examiner—K. Cochrane Carlson
Attorney, Agent, or Firm—Cushman, Darby & Cushman

[57] ABSTRACT

Derivatives of naturally occurring G-CSF having at least one of the biological properties of naturally occurring G-CSF, and a solution stability of at least 35% at 5 mg/ml are disclosed in which the derivative has at least $Cys^{17}$ of the native sequence replaced by a $Ser^{17}$ residue and $Asp^{27}$ of the native sequence replaced by a $Ser^{17}$ residue. Nucleotide sequences coding for part or all of the amino acid sequence of the derivatives of the invention may be incorporated into autonomously replicating plasmid or viral vectors employed to transform or transfect suitable procaryotic or eucaryotic host cells such as bacteria, yeast or vertebrate cells in culture.

4 Claims, 17 Drawing Sheets

Fig. 1.

```
EcoR1
AATTCTGGCA AATATTCTGA AATGAGCTGT TGACAATTAA TCATCGAACT        50
    GACCGT TTATAAGACT TTACTCGACA ACTGTTAATT AGTAGCTTGA        46

HpaI
AGTTAACTAG TACGCAAGTT CACGTAAAAA GGGTATCGAC                   90
TCAATTGATC ATGCGTTCAA GTGCATTTTT CCCATAGCTG                   86

KpnI    BamHI    XbaI    SalI    PstI    SphI
AATGGTACCC GGGGATCCTC TAGAGTCGAC CTGCAGGCAT GCAAGCTTAG        140
TTACCATGGG CCCCTAGGAG ATCTCAGCTG GACGTCCGTA CGTTCGAATC        136

ClaI
CCCGCCTAAT GAGCGGGCTT TTTTTTAT                                168
GGGCGGATTA CTCGCCCGAA AAAAAATAGC                              166
```

FIG. 2A

```
     EcoRI ScaI
AATTCAGT ACT CCA CTG GGT CCA GCA AGC TCT CTG                        59
    GTCA TGA GGT GAC CCA GGT CGT TCG AGA GAC
         Thr Pro Leu Gly Pro Ala Ser Ser Leu
          1                   5

CCG CAG TCTTTC CTG CTG AAG TGT
GGC GTC AGA AAG GAC GAC TTC ACA
Pro Gln Ser Phe Leu Leu Lys Cys
 10                      15
              SnabI
CTC GAA CAG GTA CGT AAA ATT CAA GGC GAT GGT
GAG CTT GTC CAT GCA TTT TAA GTT CCG CTA CCA                        119
Leu Glu Gln Val Arg Lys Ile Gln Gly Asp Gly
         20                      25
                         FspI
GCG GCT CTG CAG GAA AAG CTT TTC GAC ACG CGT TGC GCA
CGC CGA GAC GTC CTT TTC GAA AAG CTG TGC GCA CGT
Ala Ala Leu Gln Glu Lys Leu Phe Asp Thr Arg Cys Ala
         30                      35
              MstII
ACC TAC AAA CTG TGC CAC CCT GAG GAA CTG GTG
TGG ATG TTT GAC ACG GTG GGA CTC CTT GAC CAC
Thr Tyr Lys Leu Cys His Pro Glu Glu Leu Val
         40                      45
```

FIG. 2B

```
                          BamHI
CTG CTC GGT CAC TCT CTG GGG ATC CCG                                      179
GAC GAG CCA GTG AGA GAC CCC TAG GGC
Leu Leu Gly His Ser Leu Gly Ile Pro
            50                  55

SacI                    HindIII
TGG GCT CCA CTG AGC TCT TGC CCG TCC CAA GTC
ACC CGA GGT GAC TCG AGA ACG GGC AGG GTT CGA
Trp Ala Pro Leu Ser Ser Cys Pro Ser Gln Ala
        60                  65

TTA CAA CTG GCA GGC TGC TTG AGC CAG                                      219
AAT GTT GAC CGT CCG ACG AAC TCG GTC
Leu Gln LeuAla Gly Cys Leu Ser Gln
            70                  75

CTG CAC TCC GGT CTG TTC CTG TAC CAG GGT CTG
GAC GTG AGG CCA GAC AAG GAC ATG GTC CCA GAC
Leu His Ser Gly Leu Phe Leu Try Gln Gly Leu
        80                      85

XbaI
CTG CAG GCT CTA GAA GGC ATC TCT CCT                                      299
GAC GTC CGA GAT CTT CCG TAG AGA GGA
Leu Gln Ala Leu Glu Gly Ile Ser Pro
            90                  95
```

FIG. 2C

```
GAA TTG GGG CCC ACC CTG GAC ACA CTG CAG CTG
CTT AAC CCC GGG TGG GAC CTG TGT GAC GTC GAC
Glu Leu Gly Pro Thr Leu Asp Thr Leu Gln Leu
        100                 105
                                                        359

NdeI
GAC GTT GCC GAC TTC GCT ACT ATA ACC ATA
CTG CAA CGG CTC AAG CGA TGA TGG TAT
Asp Val Ala Asp Phe Ala Thr Trp Thr Ile
        110                 115

TGG CAA CAG ATG GAG GAA CTG GGT ATG GCT CCG
ACC GTT GTC TAC CTC CTT GAC CCA TAC CGA GGC
Trp Gln Met Glu Glu Leu Gly Met Ala Pro
        120                 125
                                                        419

GCA CTG CAG CCG ACT CAG GGT GCG ATG
CGT GAC GTC GGC TGA GTC CCA CGC TAC
Ala Leu Gln Pro Thr Gln Gly Ala Met
        130                 135

BssHII
CCA GCA TTC GCC TCT GCT TTC CAG CGG CGC GCA
GGT CGT AAG CGG AGA CGA AAG GTC GCC GCG CGT
Pro Ala Phe Ala Ser Ala Phe Gln Arg Arg Ala
        140                 145

GGC GGT GTT CTG GTT GCC TCC CAT CTT
CCG CCA CAA GAC CAA CGG AGG GTA GAA
Gly Gly Val Leu Val Ala Ser His Leu
        150                 155
                                                        479
```

FIG. 2D

```
                XhoI
CAG AGC TTC CTC GAG GTG TCT TAC CGC GTT CTG
GTC TCG AAG GAG CTC CAC AGA ATG GCG CAA GAC
Gln Ser Phe Leu Glu Val Ser Tyr Arg Val Leu
        160                 165

SalI
CGT CAC CTG GCC CAG CCG TAA G           534
GCA GTG GAC CGG GTC ATT CAGCT
Arg His Leu Ala Gln Pro
        170         174
```

FIG. 3A

EcoRI ScaI

```
AATTCAGT ACT CCA CTG GGT CCA GCA AGC TCT CTG                    59
    GTCA TGA GGT GAC CCA GGT CGT TCG AGA GAC
         Thr Pro Leu Gly Pro ala Ser Ser Leu
          1                5

CCG CAG TCT TTC CTG CTG AAG TCT
GGC GTC AGA AAG GAC GAC TTC AGA
Pro Gln Ser Phe Leu Leu Lys Ser
10                  15
                SnabI
CTC GAA CAG GTA CGT AAA ATT CAA GGC AGC GGT
GAG CTT GTC CAT GCA TTT TAA GTT CCG TCG CCA
Leu Glu Gln Val Arg Lys Ile Gln Gly Ser Gly
         20                  25
                              FspI
GCG GCT CTG CAG GAA AAG CTG TGC GCA                             119
CGC CGA GAC GTC CTT TTC GAC ACG CGT
Ala Ala Leu Gln Glu Lys Leu Cys Ala
30                  35
```

FIG. 3B

```
                                      MstII
ACC TAC AAA CTG TGC CAC CCT GAG GAA CTG GTG
TGG ATG TTT GAC ACG GTG GGA CTC CTT GAC CAC
Thr Tyr Lys Leu Cys His Pro Glu Glu Leu Val
        40                45                            179

BamHI
CTG CTC GGT CAC TCT CTG GGG ATC CCG
GAC GAG CCA GTG AGA GAC CCC TAG GGC
Leu Leu Gly His Ser Leu Gly Ile Pro
        50                55

SacI                            HindIII
TGG GCT CCA GAG TCT TGC CCG TCC CAA GCT
ACC CGA GGT GAC TCG AGA ACG GGC AGG GTT CGA
Trp Ala Pro Glu Ser Cys Pro Ser Arg Val Ala
        60                65                            219

TTA CAA CTG GCA GGC TGC TTG AGC CAG
AAT GTT GAC CGT CCG ACG AAC TCG GTC
Leu Gln Leu Ala Gly Cys Leu Ser Gln
        70                75

CTG CAC TCC GGT CTG TTC CTG TAC CAG GGT CTG
GAC GTG AGG CCA GAC AAG GAC ATG GTC CCA GAC
Leu His Ser Gly Leu Phe Leu Tyr Gln Gly Leu
        80                85

XbaI
CTG CAG GCT CTA GAA GGC ATC TCT CCT
GAC GTC CGA GAT CTT CCG TAG AGA GGA
Leu Gln Ala Leu Glu Gly Ile Ser Pro
        90                95                            299
```

FIG. 3C

```
GAA TTG GGG CCC ACC CTG GAC ACA CTG CAG CTG
CTT AAC CCC GGG TGG GAC CTG TGT GAC GTC GAC
Glu Leu Gly Pro Thr Leu Asp Thr Leu Gln Leu
        100                 105                      359

NdeI
GAC GTT GCC GAC TTC GCT ACT ACC ATA
CTG CAA CGG CTG AAG CGA TGA TGG TAT
Asp Val Ala Asp Phe ala Thr Thr Ile
        110                 115

TGG CAA CAG ATG GAG GAA CTG GAC CTG GGT ATG GCT CCG
ACC GTT GTC TAC CTC CTT GAC CTT GAC CCA TAC CGA GGC
Trp Gln Gln Met Glu Glu Leu Asp Leu Gly Met Ala Pro
        120                 125                      419

GCA CTG CAG CCG ACT CAG GGT GCG ATG
CGT GAC GTC GGC TGA GTC CCA CGC TAC
Ala Leu Gln Pro Thr Gln Gly Ala Met
        130                 135
```

FIG. 3D

```
                                                           BssHII
CCA GCA TTC GCC TCT GCT TTC CAG CGG CGC GCA
GGT CGT AAG CGG AGA CGA AAG GTC GCC GCG CGT
Pro Ala Phe Ala Ser Ala Phe Gln Arg Arg Ala
140                         145

GGC GGT GTT CTG GTT GCC CGG TCC CAT CTT                    479
CCG CCA CAA GAC CAA CGG AGG GTA GAA
Gly Gly Val Leu Val Ala Ser His Leu
150                         155
              XhoI
CAG AGC TTC CTC GAG GTG TCT TAC CGC GTT
GTC TCG AAG GAG CTC CAC AGA ATG GCG CAA
Gln Ser Phe Leu Glu Val Ser Tyr Arg Val
160                         165
                    SalI
CTG CGT CAC CTG GCC CAG CCG TAA G          534
GAC GCA GTG GAC CGG GTC GGC ATT CAGCT
Leu Arg His Leu Ala Gln Pro
170             174
```

FIG.4A

TRANSCRIPTION TERMINATION SEQUENCE

<u>Sal</u>I
5' TCGACATTATATTACTAATTAATTGGGGACCCTAGAGGTCCCCTTTTTTATTTTAA
3'     GTAATATAATGATTAATTAACCCCTGGGATCTCCAGGGGAAAAAATAAAATT

Sp<u>h</u>I HindIII
AAAGCATGCA            3'
TTTCGTACGTTCGA        5'

FIG.4B

<u>Sal</u>I
5' TCGACATTATATTACTAATTAATTGGGGACCCTAGAGGTCCCCTTTTTTATTTTAA
3'     GTAATATAATGATTAATTAACCCCTGGGATCTCCAGGGGAAAAAATAAAATT

SphI Ba<u>m</u>HI  St<u>y</u>I
AAAGCATGCGGATCCC         3'
TTTCGTACGCCTAGGGGAAC     5'

EcoRI
AATTCTGGCA AATATTCTGA AATGAGCTGT TGACAATTAA TCATCGAACT

HpaI
AGTTAACTAG TACGCAGAGC TCAATCTAGA GGGTATTAAT AATGTTCCCA

TTGGAGGATG ATTAATG

POLYPEPTIDE DERIVATIVES OF GRANULOCYTE COLONY STIMULATING FACTOR

The present invention relates to derivatives of granulocyte colony stimulating factor (G-CSF) having good solution stability and to processes for their preparation as well as to pharmaceutical compositions containing them.

The colony stimulating factors are a class of protein hormones which stimulate the proliferation and the function of specific blood cell types such as granulocytes. Granulocytes engulf and devour microbial invaders and cell debris and thus represent a vital factor in response to infection. In this regard granulocytes can extend pseudopods and slip out of the vascular tree between the lining endothelial cells. The neutrophilic granulocytes can then come into direct contact with the microorganisms and destroy them using unique enzyme systems such as those which generate superoxide anions. Since granulocytes have only a short life span in the circulation (approximately 6–12 hours) and are destroyed in the course of their function, it is necessary for the stem cells of the bone marrow to generate as many granulocytes as red blood cells each day. Further, this rate of production of granulocytes needs to increase enormously if the demands of infection are to be met. As a result of their fast turnover, the granulocyte count falls rapidly if the bone marrow is damaged for example by cancer chemotherapy, radiation, AIDS or haematological disorders and patients become liable to overwhelming infection. Indeed sepsis is a common cause of death in cancer patients whose marrow is suppressed by radiation treatment, chemotherapy or their neoplastic disease.

Granulocyte colony stimulating factor (G-CSF) has been described in the literature by Wallet K. et al Proc. Natl. Acad. Sci. U.S.A Vol 82, pp 1526–1530 and has also been described in European Patent Publication No 169,566 and PCT Patent Publication No WO 87/01132. G-CSF has been shown to stimulate granulocyte production in vivo and to function with minimal side effects. As a result human G-CSF is seen as having potential utility in the management of neutropaenia associated with chemotherapy, radiation therapy, radiation accident or autologous bone marrow transplantation. Moreover G-CSF may have utility in the stimulation of bone marrow suppression associated with AIDS, in the treatment of myelodysplastic syndromes characterised by granulocyte functional abnormalities and as an adjunct to the treatment of severe injections.

In addition to the above certain analogues of G-CSF have been described in PCT Patent Publication No WO 87/01132, in European Patent Publication No 243,153, in European Patent Publication No 256,843, in European Patent Publication No 272,703 and in Biochemical and Biophysical Research Communication [1989] Vol. 159, No 1, pp 103–111 Kuga T. et al. Furthermore, modification of G-CSF and [Ser$^{17}$]G-CSF has been effected by substituting the cysteine and serine residues at position 17, but such changes failed to achieve the desired effect (Protein Engineering, Vol 3. No.4 page 360 (1990)).

G-CSF and the analogues referred to above tend to suffer from solution instability in that on standing they tend to precipitate out of solution thus resulting in short shelf life and problems in storage at high concentrations. Moreover G-CSF and certain of the analogues referred to above have a tendency to covalent aggregation on storage.

The present invention is based on the discovery of modifications that may be made to a G-CSF or a derivative thereof having part or all of the amino acid sequence and at least one of the biological properties of naturally occurring G-CSF, for example of naturally occurring human G-CSF, whereby to improve solution stability.

Thus according to one feature of the present invention there is provided a derivative of naturally occurring G-CSF having at least one of the biological properties of naturally occurring G-CSF and a solution stability (as herein defined) of at least 35% at 5 mg/ml, the said derivative having at least Cys$^{17}$ of the native sequence replaced by a Ser$^{17}$ residue and Asp$^{27}$ of the native sequence replaced by a Ser$^{27}$ residue.

The derivatives of the present invention may conveniently have at least one further modification selected from:

a) Glu$^{11}$ of the native sequence replaced by an Arg$^{11}$ residue;

b) Leu$^{15}$ of the native sequence replaced by a Glu$^{15}$ residue;

c) Lys$^{23}$ of the native sequence replaced by an Arg$^{23}$ residue;

d) Gly$^{26}$ of the native sequence replaced by an Ala$^{26}$ residue;

e) Gly$^{28}$ of the native sequence replaced by an Ala$^{28}$ residue;

f) Ala$^{30}$ of the native sequence replaced by an Lys$^{30}$ or Arg$^{30}$ residue;

g) Lys$^{34}$ of the native sequence replaced by an Arg$^{34}$ residue;

h) Lys$^{40}$ of the native sequence replaced by an Arg$^{40}$ residue;

i) Pro$^{44}$ of the native sequence replaced by an Ala$^{44}$ residue;

j) Leu$^{49}$ of the native sequence replaced by a Lys$^{49}$ residue;

k) Gly$^{51}$ of the native sequence replaced by an Ala$^{51}$ residue;

l) Gly$^{55}$ of the native sequence replaced by an Ala$^{55}$ residue;

m) Trp$^{58}$ of the native sequence replaced by a Lys$^{58}$ residue;

n) Pro$^{60}$ of the native sequence replaced by a Ser$^{60}$ residue;

o) Pro$^{65}$ of the native sequence replaced by a Ser$^{65}$ residue;

p) Pro$^{111}$ of the native sequence replaced by a Glu$^{111}$ residue;

q) Thr$^{115}$ of the native sequence replaced by a Ser$^{115}$ residue;

r) Thr$^{116}$ of the native sequence replaced by a Set$^{116}$ residue; and s) Tyr$^{165}$ of the native sequence replaced by an Arg$^{165}$ residue.

The presence of at least one further modification selected from (b) to (s) is preferred, but the presence of at least one further modification selected from (b), (d), (e), (f), (n) and (o) is particularly preferred of which further modification (o) is especially preferred.

More preferably the further modification comprises at least one of the following:

i) Gln$^{11}$, Pro$^{60,65}$ of the native sequence replaced by Arg$^{11}$, Ser$^{60,65}$;

ii) Ala$^{111}$, Thr$^{115,116}$ of the native sequence replaced by Glu$^{111}$, Ser$^{115,116}$;
iii) Gln$^{11}$, Trp$^{58}$, Tyr$^{165}$ of the native sequence replaced by Arg$^{11,165}$, Lys$^{58}$;
iv) Leu$^{15}$, Gly$^{26,28}$, Ala$^{30}$ of the native sequence replaced by Glu$^{15}$, Ala$^{26,28}$, Lys$^{30}$; or
v) Asp$^{27}$, Pro$^{44}$, Leu$^{49}$, Gly$^{51,55}$, Tr$^{58}$ of the native sequence replaced by Lys$^{49,58}$, Ala$^{44,51,55}$.

The further modification may also, preferably comprise at least one of the following:
vi) Leu$^{15}$, Gly$^{26,28}$, Ala$^{30}$ of the native sequence replaced by Glu$^{15}$, Ala$^{26,28}$, Arg$^{30}$; or
vii) Pro$^{65}$ of the native sequence replaced by Ser65; or
viii) Pro$^{60,65}$ of the native sequence replaced by Ser60,65; or
ix) Gln$^{11}$, Pro$^{65}$ of the native sequence replaced by Arg$^{11}$,Ser$^{65}$.

The above defined modifications may thus, if desired, be introduced into any polypeptide having at least one of the biological properties of naturally occurring G-CSF in order to improve the solution stability of the molecule. The modifications of the present invention may thus be applied to such polypeptides which differ in amino acid sequence from that specified herein for the naturally occurring G-CSFs in terms of the identity or location of one or more residues (for example substitutions, terminal and internal additions and deletions). As examples such polypeptides might include those which are foreshortened, for example by deletions; or those which are more stable to hydrolysis (and, therefore, may have more pronounced or longer lasting effects than naturally occurring); or which have been altered to delete one or more potential sites for 0-glycosylation (which may result in higher activities for yeast-produced products); or which have one or more cysteine residues deleted or replaced, for example by alanine or serine residues and are potentially more easily isolated in active form from microbial systems; or which have one or more tyrosine residues replaced by phenylalanine and may bind more or less readily to human G-CSF receptors on target cells. The proposed modifications (a) to (s), preferably (i) to (ix) may thus, for example be applied to either native G-CSF having Cys$^{17}$ of the native sequence replaced by Ser$^{17}$ or to allelic variants and analogues thereof known to possess at least one of the biological properties of naturally occurring G-CSF such as those described in the publications referred to above.

Polypeptides of the present invention that have been tested have been found to possess improved solution stability over the corresponding unmodified polypeptide whilst either retaining significant biological activity or even having improved biological activity.

It will be understood from the above that the property of solution stability is different from that of solubility. Solution stability is the decreased tendency of a substance to precipitate from solution under physiological conditions of pH, temperature and ionic strength.

Solution stability is measured herein by determining the percentage of G-CSF derivative remaining in solution in phosphate buffered saline after 14 days at 37° C. given an initial concentration of 1 mg/ml, 5 mg/ml and/or 10 mg/ml. Measurement of solution stability is described in detail hereinafter in Reference Example 4. Conveniently polypeptides of the present invention will have a solution stability at 5 mg/ml of at least 35%, advantageously at least 50% and preferably at least 75%. Preferably the polypeptides of the present invention will have a solution stability at 10 mg/ml of at least 75%, especially at least 85%.

The expression "naturally occurring G-CSF" as used herein refers to those G-CSFs that have been found to exist in nature and includes the two polypeptides having the amino acid sequence set out in SEQ ID No37. These two polypeptides differ only in so far as a tripepride insert Val-Ser-Glu is present in one polypeptide between positions 35 and 36, but absent in the other. The numbering system used throughout the present specification is based on the naturally occurring polypeptide without the Val-Ser-Glu insert and the term "native" as used herein refers to this polypeptide without the Val Ser Glu insert. It will be appreciated that the present invention is applicable to all naturally occurring forms of G-CSF and analogues thereof as described above and consequential revision of the position numbers of the polypeptide may be necessary depending on the form of naturally occurring G-CSF selected for modification.

According to a further feature of the present invention there is provided a DNA sequence encoding all or part of the amino acid sequence of a derivative of naturally occurring G-CSF as hereinbefore defined. Such sequences may, for example include 1) the incorporation of codons preferred for expression by selected non-mammalian hosts; 2) the provision of sites for cleavage by restriction endonucleases; and/or 3) the provision of additional initial, terminal or intermediate DNA sequences which facilitate construction of readily expressed vectors. The DNA sequences of the present invention include those useful in securing expression in procaryotic or eucaryotic host cells and the derivatives of the present invention may be in either glycosylated or non-glycosylated form depending upon the host cell selected. Where the derivative of the present invention is obtained in non-glycosylated form, for example following expression in procaryotic host cells, the derivative may, if desired, be glycosylated chemically for example with mammalian or other eucaryotic carbohydrates.

According to a further feature of the present invention there is provided a recombinant vector containing a DNA sequence as hereinbefore defined. The recombinant vector may for example be a biologically functional plasmid or viral DNA vector.

According to a further feature of the present invention there is provided a process for the preparation of a recombinant vector as hereinbefore defined which comprises inserting a DNA sequence as hereinbefore defined into a vector.

According to a further feature of the present invention there is provided a procaryotic or eucaryotic host cell stable transformed or transfected with a recombinant vector as hereinbefore defined.

According to a further feature of the present invention there is provided a process for the preparation of a procaryotic or eucaryotic host cell as hereinbefore defined which comprises transforming or transfecting a procaryotic or eucaryotic cell with a recombinant vector as hereinbefore defined whereby to yield a stably transformed or transfected procaryotic or eucaryotic host.

According to a further feature of the present invention there is provided a process for the preparation of a derivative of naturally occurring G-CSF of the present invention which comprises culturing a procaryotic or eucaryotic host cell of the invention whereby to obtain said derivative. The process will advantageously also include the step of isolating the said derivative produced by expression of the DNA sequence of the invention in the recombinant vector of the invention.

The host cells for use in processes of the present invention are preferably procaryotic such as *E.coli*, but may be yeast cells such as *Saccharomyces cerevisiae* or mammalian cells such as CHO cells (chinese hamster ovary cells).

According to a further feature of the present invention there is provided a pharmaceutical composition comprising as active ingredient at least one derivative of naturally occurring G-CSF of the present invention in association with a pharmaceutically acceptable carrier or excipient.

According to a further feature of the present invention there is provided a method for providing haematopoietic therapy to a mammal which comprises administering an effective amount of a derivative of the present invention.

According to a further feature of the present invention there is provided a method for arresting the proliferation of leukaemic cells which comprises administering an effective amount of a derivative of the present invention.

BRIEF DESCRIPTION OF THE DRAWINGS

FIG. 1 shows the nucleotide sequence of the 167 bp fragment referred to in Example 1;

FIGS. 2A–D (hereinafter collectively referred to as FIG. 2) show the amino acid sequence and corresponding nucleotide sequence of native human (hu) G-CSF and restriction sites;

FIGS. 3A–D (hereinafter collectively referred to as FIG. 3) show the amino acid sequence and corresponding nucleotide sequence of [Ser$^{17,27}$] hu G-CSF and restriction sites.

FIGS. 4a and b shows the nucleotide sequence of the T4 transcription terminator having (a) terminal SalI and HindIII restriction sites; and (b) terminal SalI and StyI restriction sites;

DETAILED DESCRIPTION

Figure 5:
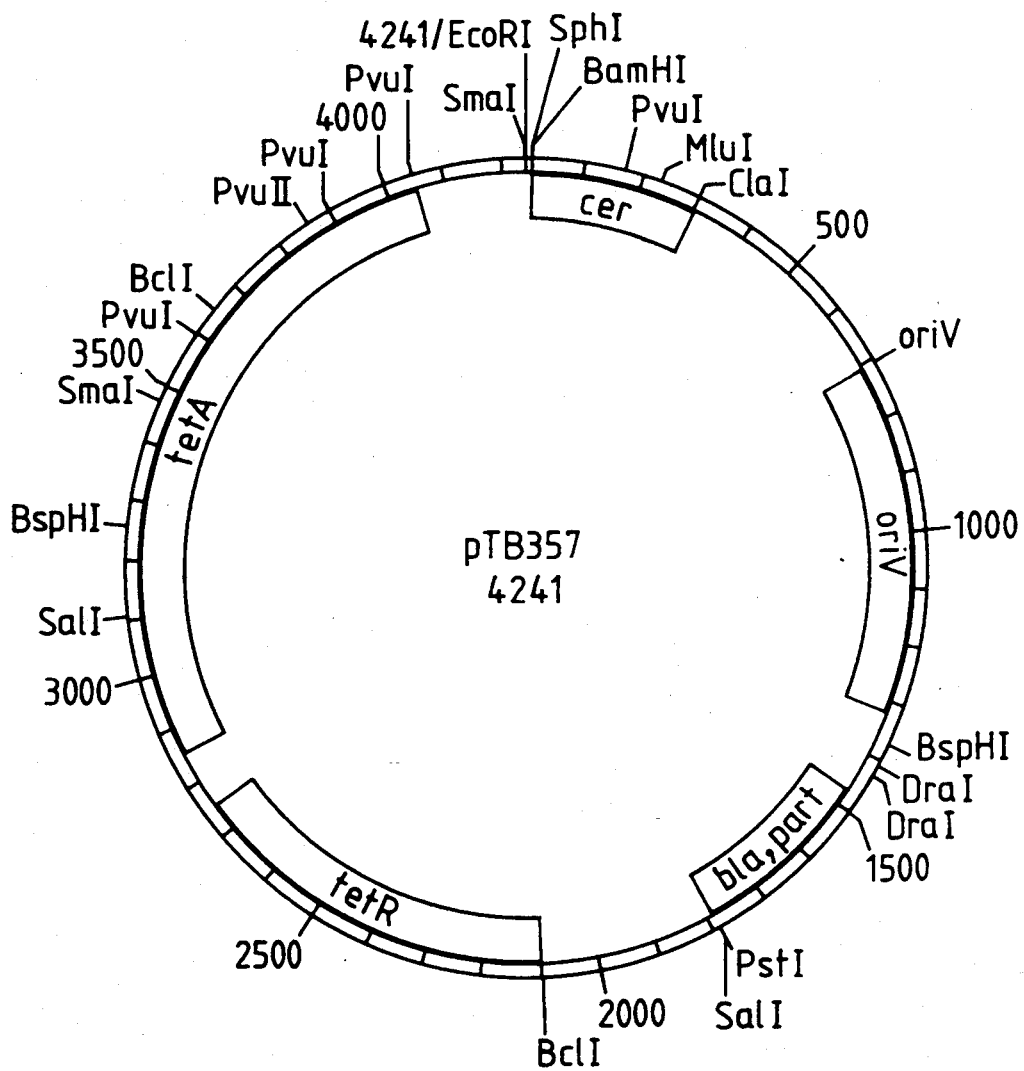
FIG. 5 shows a restriction map of pTB357 (also referred to herein as pLB004)

Advantageously the derivatives of the present invention are selected to possess one of the further modifications (i), (ii), (iii), (iv), (v), (vi), (vii), (viii) or (ix) or as hereinbefore defined, preferably one of the further modifications (i), (ii), (iv), (vi), (vii), (viii) or (ix) and especially further modification (ii), (iv), (vi), (vii), (viii) or (ix).

Particularly preferred derivatives according to the present invention by virtue of their good solution stability include

[Arg$^{11}$, Ser$^{17,27,60,65}$]G-CSF;
[Glu$^{15}$, Ser$^{17,27}$, Ala$^{26,28}$, Lys$^{30}$]G-CSF;
[Arg$^{11}$, Glu$^{15}$, Ser$^{17,27,60,65}$, Ala$^{26,28}$, Lys$^{30}$]G-CSF
[Arg$^{11,23}$,Ser$^{17,27,60,65}$]G-CSF
[Arg$^{11,34}$,Ser$^{17,27,60,65}$]G-CSF
[Arg$^{11,40}$,Ser$^{17,27,60,65}$]G-CSF
[Ala$^{1}$,Thr$^{3}$,Tyr$^{4}$,Arg$^{5,11}$,Ser$^{17,27,60,65}$]G-CSF
[Arg$^{11}$,Glu$^{15,111}$,Ser$^{17,27,60,65,115,116}$,Ala$^{26,28}$,Lys$^{30}$]G-CSF
[Arg$^{11,165}$,Glu$^{15}$,Ser$^{17,27,60,65}$,Ala$^{26,28}$,Lys$^{30,58}$]G-CSF
[Arg$^{11}$,Glu$^{15}$,Ser$^{17,27,60,65}$,Ala$^{26,28,44,51,55}$,Lys$^{30,49,58}$]G-CSF
[Arg$^{11,165}$,Glu$^{15,111}$,Ser$^{17,27,60,65,115,116}$,Ala$^{26,28,44,51,55}$,Lys$^{30,49,58}$]G-CSF
[Glu$^{15}$,Ser$^{17,27}$,Ala$^{26,28}$,Arg$^{30}$]hu G-CSF

Especially preferred derivatives of the invention by virtue of their excellent solution stability and good specific acitivity include:

i) [Arg$^{11}$,Ser$^{17,27,60,65}$]G-CSF,
ii) [Glu$^{15}$,Ser$^{17,27}$,Ala$^{26,28}$,Lys$^{30}$]G-CSF,
iii) [Arg$^{11}$,Glu$^{15}$,Ser$^{17,27,60,65}$,Ala$^{26,28}$,Lys$^{30}$]G-CSF,
iv) [Arg$^{11,40}$,Ser$^{17,27,60,65}$]G-CSF,
v) [Arg$^{11,23}$,Ser$^{17,27,60,65}$]G-CSF,
vi) [Arg$^{11,165}$,Glu$^{15}$,Ser$^{17,27,60,65}$,Ala$^{26,28}$,Lys$^{30,58}$]hu G-CSF
vii) [Arg$^{11}$,Glu$^{15,111}$,Ser$^{17,27,60,65,115,116}$,Ala$^{26,28}$,Lys$^{30}$]hu G-CSF,
viii) [Glu$^{15}$,Ser$^{17,27}$,Ala$^{26,28}$,Arg$^{30}$]hu G-CSF, and
ix) [Ala$^{1}$,Thr$^{3}$,Tyr$^{4}$,Arg$^{5,11}$,Ser$^{17,27,60,65}$]G-CSF
x) [Ser$^{17,27,60,65}$]hu G-CSF,
xi) [Arg$^{11}$,Ser$^{17,27,65}$]hu G-CSF, and
xii) [Ser$^{17,27,65}$]hu G-CSF of which (i), (ii), (iii), (vi), (vii), (viii) and (xii) are most preferred.

These latter human G-CSF derivatives show not only excellent solution stability properties, but also possess improved specific activity over naturally occurring human G-CSF.

A presequence methionine may be either present or absent in the polypeptides of the present invention but is conveniently present.

It has been found advantageous to employ a production vector based on pAT153, comprising:

i) a promoter and where appropriate an operator therefor, for example a trp promoter or a T7A3 promoter. The T7A3 promoter is the A3 promoter of bacteriophage T7 [see Dunn J. J. and Studier F. W. J. Mol. Biol. 166, 477–535 (1983)]. The complete nucleotide sequence of bacteriophage T7 DNA and the locations of T7 genetic elements are set out in this reference;

ii) a ribosome binding site sequence, for example a trp leader ribosome binding site sequence;

iii) a cloning site for the gene to be expressed;

iv) a T4 transcription termination sequence (see SEQ ID No. 51 and FIG. 4)

v) a cer sequence (Summers D. et al MGG, 201, p334–338, 1985)

vi) a tetracycline repressor gene (Tet R)

vii) tetracycline resistance gene (Tet A)

viii) multiple restriction enzyme recognition sequences

SEQ ID No 50. sets out a sequence which includes an EcoRI restriction endonuclease site (nucleotides 1–6), the A3 promoter sequence (nucleotides 7–52), the trp leader ribosome binding site sequence (nucleotides 53–78) and the translation initiation codon (nucleotides 79–81)

It may be advantageous to cultivate the host capable of expressing a derivative of the invention, in a growth medium and adding a supplement which includes yeast extract to the growth medium during cultivation. It is preferable that addition of the supplement which includes yeast extract is initiated at a predetermined time after the start of cultivation. The rate of addition of the supplement which comprises yeast extract is preferably such that the growth medium does not become exhausted of yeast extract. This is particularly advantageous where the production vector is used with a T7A3 promoter.

It may also be advantageous to cultivate a host, transformed with a recombinant vector carrying genetic material coding for a derivative of the present invention, in the presence of leucine and/or threonine in an amount sufficient to give improved accumulation of the derivative of the present invention. Thus it is particularly advantageous to effect the fermentation in the presence of leucine where the production vector is used with the trp promoter.

In addition to the discovery of modifications that may be made to a G-CSF or derivative thereof having part or all of the amino acid sequence and at teast one of the biological properties of naturally occurring G-CSF, to improve solution stability, the present invention is further based on the discovery of modified techniques for the purification of such G-CSFs and derivatives thereof.

Thus for example there is no disclosure in PCT Patent Publication No WO 87/01132 of the removal of detergent, particularly N-lauroyl safcosine in salt form (eg. Sarkosyl) from the G-CSF analogues prepared in this PCT Publication. It was therefore necessary to identify such a technique in order that the solution stability of the G-CSF derivatives of the present invention could be assessed at high concentration and in order that formulation studies could be conducted. In one embodiment of the invention detergent removal was effected in the presence of a phosphate buffered saline (pH 7.2–7.5). The phosphate buffered saline may conveniently be prepared from isotonic saline and may thus for example have a composition as described in Example 1. In this regard it was found that other buffers were less preferred since either detergent removal, particularly N-lauroyl sarcosine (in salt form) removal, was slower or more protein precipitated out. It is further preferred to effect diafiltration, preferably at this stage, since this was found to improve efficiency without provoking increased protein precipitation. For example diafiltration was found to be preferable to conventional diffusion dialysis. Furthermore it was found that detergent concentration, particularly N-lauroyl sarcosine in salt form (eg. Sarkosyl) concentration, could be reduced below 1% whilst retaining resolution during chromatography. A reduction in initial detergent concentration assists detergent removal and thus it is preferred to use the minimum concentration of detergent, for example N-lauroyl sarcosine (in salt form eg. Sarkosyl), consistent with retaining resolution during chromatography. A particular concentration of detergent, for example N-lauroyl sarcosine (in salt form) eg. Sarkosyl, is thus from 0.8% to 0.2%, preferably from 0.5 to 0.2%, especially about 0.3%.

In addition to the above it was found that the removal of detergent such as N-lauroyl sarcosine (in salt form) e.g. Sarkosyl activates a trace of proteolytic activity which may complicate product evaluation. It has further been found that this proteolytic activity may be significantly reduced and even eliminated if, after detergent removal by diafiltration, the pH is reduced to below 7.0 before substantial proteolysis, conveniently by diafiltration and preferably by dialysis. Thus in a further embodiment of the present invention the reduction or removal of trace proteolytic acitivity may be effected at a pH that is below 7.0 but which is sufficiently high to avoid significant hydrolysis of the polypeptide. The pH is advantageously in the range 6.0 to 4.5, preferably 5.8 to 5.0 especially about 5.4. A further advantage of this embodiment of the invention is that E.coli contaminants and/or degraded or incorrectly folded protein can be precipitated by effecting this lowering of pH. It is preferred that purification include the step of size exclusion chromatography since otherwise the problem of proteolytic degradation is increased and whilst the present embodiment will reduce such degradation it makes it difficult to eliminate.

In addition to the above processes, the introduction of solution stability into a G-CSF or derivative thereof enables substantial simplification of the process of extraction. Thus according to a further feature of the present invention there is provided a process for extracting an active derivative of the invention (as hereinbefore defined) from an inclusion body thereof which comprises 1) suspending said inclusion body in a detergent, particularly N-lauroyl sarcosine in salt form (e.g. Sarkosyl) 2) oxidation, 3) removal of detergent for example as hereinbefore described and 4) maintaining solution obtained following removal of detergent at an elevated temperature for example 30°–45° C., advantageously 34°–42° C. whereby to precipitate contaminating bacterial protein, product oligomers and/or degradation products. The said solution is conveniently maintained at said elevated temperature for from 6–24 hours, advantageously 8–18 hours preferably 10–14 hours, especially about 12 hours.

The extraction process of the present invention may for example be effected by lysing host cells followed by centrifugation to obtain the inclusion body for example in the form of a pellet. The inclusion body may then be suspended in a detergent such as, for example N-lauroyl sareosine in salt form (eg Sarkosyl), preferably 1-3%, especially about 2% N-lauroyl sarcosine in salt form (eg. Sarkosyl). Suspension in detergent may be followed by oxidation, for example in the presence of copper sulphate ($CuSO_4$) which in turn may be followed by centrifugation.

Where it is possible to wash the inclusion body it is preferred to use urea rather than for example deoxycholate.

The extraction process of the present invention enables the production process to be simplified for example by elimination of the need for the use of size exclusion columns. Moreover the high recovery of product from the heat treatment step appears to be one of the advantages of the increased solution stability of the derivatives of the present invention. Indeed the greater the solution stability the more suited is the protein to the new extraction process. Thus for example it is preferred to apply this extraction process to the extraction of derivatives of the present invention having a solution stability of at least 85% at 10 mg/ml. When the known analogue [$Met^{-1}$, $Ser^{17}$] G-CSF was extracted by the above process, rpHPLC indicated that only 40% of the desired product remained in solution after heat treatment of a retentate containing 1 mg/ml total protein. At 3 mg/ml total protein, only 19% of the analogue remained in solution.

All nucleotide sequences referred to herein are specified in the conventional 5'-3' sense.

The derivatives of the present invention are based on human G-CSF which is also referred to as hu G-CSF.

Since the derivatives prepared in the Examples are all prepared using E.coli, a presequence methionine will generally be present.

The following materials are referred to hereinafter in the Reference Examples and Examples and their constitution is as follows:

The term "N-lauroyl sarcosine" as used herein refers to the use of the said substance in salt form. Thus in the Examples N-lauroyl sarcosine is used in the form of the sodium salt.

BUFFERS FOR RESTRICTION ENZYMES

Stability: stable at −20° C.
Buffer composition:

| Buffer components | Final concentration in mmol/l (1:10 diluted set buffer) | | | | |
|---|---|---|---|---|---|
| | A | B | L | M | H |
| Tris acetate | 33 | — | — | — | — |
| Tris-HCl | — | 10 | 10 | 10 | 50 |
| Mg-acetate | 10 | — | — | — | — |
| $MgCl_2$ | — | 5 | 10 | 10 | 10 |
| K-acetate | 66 | — | — | — | — |
| NaCl | — | 100 | — | 50 | 100 |
| Dithioerythritol (DTE) | — | — | 1 | 1 | 1 |
| Dithiothreitol (DTT) | 0.5 | — | — | — | — |
| 2-Mercaptoethanol | — | 1 | — | — | — |
| pH at 37° C. | 7.9 | 8.0 | 7.5 | 7.5 | 7.5 |

The above buffers are available from Boehringer Mannheim.

In the site-directed mutagenesis procedure—Reference Example 2

| Buffer 1 | 100 mM Tris HCl pH 8.0 |
| | 100 mM NaCl |
| | 20 mM $MgCl_2$ |
| Buffer 2 | 10 mM Tris HCl pH 8.0 |
| | 20 mM NaCl |
| | 1 mM EDTA |
| Buffer 3 | 12 mM Tris HCl pH 7.7 |
| | 30 mM NaCl |
| | 10 mM $MgCl_2$ |
| | 8 mM 2-mercapto ethanol |
| Buffer 4 | 60 mM Tris HCl pH 8.0 |
| | 90 mM NaCl |
| | 6 mM $MgCl_2$ |
| | 10 mM DTT |

Nucleotide mix 1 250 μM each of dATP, dGTP, dCTP=S (phosphorothioate derivative of dCTP), dTTP and 1 mM ATP Nucleotide mix 2 250 μM each of dATP, dGTP, dCTP, dTTP and 350 μM ATP M9 minimal media

| Ammonium chloride | 1 g |
| Disodium hydrogen orthophosphate | 6 g |
| Potassium dihydrogen orthophosphate | 3 g |
| Sodium chloride | 0.5 g |
| In distilled water | 1 l. |

Supplements/75ml

| 300 μl | 50% glucose |
| 75 μl | 1M $MgSO_4$ |
| 75 μl | 0.1M $CaCl_2$ |
| 75 μl | 4 mg/ml thiamine |
| 75 μl | 20% casin amino acids |

Trace Element Solution (TES)

TES has the following composition:

| $AlCl_3$ $6H_2O$ | 0.1 mg $l^{-1}$ | 100 μg $l^{-1}$ |
| $CoCl_2$ $6H_2O$ | 0.04 mg $l^{-1}$ | 40 μg $l^{-1}$ |
| $KCr(SO_4)_2 12H_2O$ | 0.01 mg $l^{-1}$ | 10 μg $l^{-1}$ |
| $CuCl_2$ $2H_2O$ | 0.01 mg $l^{-1}$ | 10 μg $l^{-1}$ |
| $H_3BO_3$ | 0.005 mg $l^{-1}$ | 5 μg $l^{-1}$ |
| KI | 0.1 mg $l^{-1}$ | 100 μg $l^{-1}$ |
| $MnSO_4H_2O$ | 0.1 mg $l^{-1}$ | 100 μg $l^{-1}$ |
| $NiSO_4$ $6H_2O$ | 0.0045 ng $l^{-1}$ | 4.5 μg $l^{-1}$ |
| $Na_2MoO_4 2H_2O$ | 0.02 mg $l^{-1}$ | 20 μg $l^{-1}$ |
| $ZnSO_4 7H_2O$ | 0.02 mg $l^{-1}$ | 20 μg $l^{-1}$ | and is added to growth media at 0.5 ml/l

Geneclean (TM)

The kit contains 1) 6M sodium iodide 2) a concentrated solution of sodium chloride, Tris and EDTA for making a sodium chloride/ethanol/water wash; 3) Glassmilk (TM)- a 1.5 ml vial containing 1.25 ml of a suspension of silica matrix in water.

This is a technique for DNA purification based on the method of Vogelstein and Gillespie published in Proceedings of the National Academy of Sciences USA (1979) Vol 76, p 615.

Alternatively any of the methods described in "Molecular Cloning—a laboratory manual" Second Edition, Sambrook, Fritsch and Maniatis (Cold Spring Harbor Laboratory, 1989) can be used.

Random Label Kit Product of Pharmacia No 27-9250

The procedure is described in "Molecular Cloning—a Laboratory Manual" Second Edition, Sambrook, Fritsch and Maniatis, pp 10.13–10.17 (Published by Cold Spring Harbor Laboratory 1989).

Sequenase (TM)

Chemically modified T7 DNA polymerase

Based on the procedure of Tabor and Richardson published in "Proceedings of the National Academy of Sciences USA (1987) vol 84 pp 4767–4771.

T4 DNA ligase

Described in "Molecular Cloning—a Laboratory Manual" Second Edition, Sambrook, Fritsch and Maniatis 5.60–5.64 (Published by Cold Spring Harbor Laboratory 1989) and also by Weiss B. et al J. Biol. Chem. Vol 243 p 4543 (1968).

The following non-limiting Examples are given by way of illustration only.

EXAMPLE 1

Preparation of [$Ser^{17,27}$] human G-CSF

The procedure for steps a) and b) in Reference Example 1 was repeated with the following modifications:

Oligonucleotides SEQ ID Nos 24, 25, 26 and 27 (as hereinafter defined) replace SEQ ID Nos 1, 2, 3 and 4 (as hereinafter defined) respectively.

c) Cloning of the gene for [Ser$^{17,27}$] human G-CSF into an expression vector The gene described above (see FIG. 3 and SEQ ID No. 49) was cloned into plasmid vector pICI0020. This vector is a pAT153 based plasmid in which the 651 bp EcoRI-AccI region is replaced by a 167 bp EcoRI - ClaI fragment (SEQ ID No.47) consisting of:

(1) a synthetic *E. coli* trp promoter and trp leader ribosome binding site (2) a translation initiation codon (3) a multiple restriction enzyme recognition sequence derived from M13mp18, containing sites for KpnI, BamHI, XbaI, SalI, PstI, SphI and HindIII (4) a synthetic transcription termination sequence The DNA sequence of this region is shown in FIG. 1. (SEQ ID: 47 and SEQ ID NO:60)

The pICI0020 expression vector was digested to completion with KpnI (BCL) in 10mM Tris HCl (pH7.5), 10 mM magnesium chloride. The DNA was precipitated with ethanol at −20° C. from a solution containing 0.3 M sodium acetate and then the 3'- sticky ends were removed by treatment with T4 DNA polymerase for 10 minutes at 37° C. as follows:

DNA (1 μg) in water (16 μl)
10X T4 polymerase buffer (2 μl)
0.33 M Tris acetate pH7.9
0.1M Magnesium acetate
0.66M Potassium acetate
5 mM dithiothreitol
1 mg/ml bovine serum albumin (BSA PENTAX fraction V)
2 mM dNTP mixture (1 μl)
T4 DNA polymerase (1 μl; 2.5 units/μl BCL)

Water (80 μl) was added and the mixture extracted with phenol/chloroform (100 μl) and then with chloroform (100 μl). The DNA was precipitated with ethanol (250 μl) at −20° C. after addition of 3M sodium acetate (10 μl) then digested to completion with SalI (BCL) in 150 mM NaCl, 10 mM MgCl$_2$ and 10 mM Tris HCl (pH7.5). The Kpn-blunt ended to SalI vector was purified from a 0.7% agarose gel and isolated by use of Geneclean (trademark) following the manufacturer's (Bio101, USA) recommended procedure.

The synthetic gene was isolated from the pSTP1 vectors as follows. The vectors were digested with ScaI and SalI (both from BCL) in 100 mM Nacl, 10 mM MgCl$_2$ and 10 mM Tris HCl (pH7.5). The 530 bp fragment was purified from a 0.7% agarose gel and isolated by use of Geneclean (trademark) following the manufacturer's (Bio101) recommended procedure.

For ligation, a mixture of the ScaI - SalI gene fragment (50 ng) and the pICI0020 vector fragment (100 ng) in 20 μl of a solution containing 50 mM Tris HCl (pH7.6), 10 mM MgCl$_2$, 1 mM ATP, 1 mM DTT, 5% w/v PEG 8000 and T4 DNA ligase (2 units; BRL) were incubated at 16° C. for 20 hours. The resulting mixture was used to transform competent *E. coli* HB101 cells (as supplied by BRL) as described herein. Transformants were selected for by growth on L-agar plates containing 50 μg/ml ampicillin and screened for the presence of the gene by colony hybridisation with a $^{32}$p labelled probe (SEQ ID No 24) as described herein. Plasmid DNA was prepared from 6 positively hybridising colonies, purified by centrifugation in a caesium chloride gradient and the sequence confirmed by dideoxy sequencing as described herein.

The plasmid containing this gene was designated pICI 1080.

d) Subcloning of an expression cassette containing a gene for [Ser$^{17,27}$]G-CSF into M13mp18.

The following subcloning was effected to provide a starting point for preparation of the G-CSF derivatives detailed in Examples 3–8.

Plasmid DNA from pICI1080 (purified by caesium chloride density centrifugation) was digested to completion with EcoRI and SalI (BCL) according to the manufacturer's instructions. The small EcoRI-SalI fragment containing the trp promoter and [Ser$^{17,27}$]G-CSF gene was isolated from a 0.7% agarose gel by use of Geneclean (trademark). This fragment was cloned into an EcoRI-SalI cut M13mp18 vector (DNA supplied by Amersham International; enzymes from BCL). The fragments were ligated together in 5× BRL ligation Buffer using BRL T4 DNA ligase (described previously). The ligation mix was used to transfect competent *E. coli* TG1 cells (made competent according to the calcium chloride method of Mandel and Higa described in Molecular Cloning—A Laboratory Manual—Maniatis et al Cold Spring Harbor). The transfected cells were suspended in TY top agar containing 2% X-Gal in DMF and 200 μl log phase *E. coli* TG1 cells and were plated on 2× TY agar plates (TY top agar—8 g Bactotryptone, 5 g Yeast Extract, 5 g NaCl, 3.75 g Bacto-agar in 500 μl sterile H$_2$O; TY plates—8 g Bactotryptone, 5 g Yeast-extract, 5 g NaCl, 7.5 g Bactoagar in 500 ml sterile H$_2$O.) Four white plaques were picked into 4×2 ml 1% *E. coli* TG1 cells in TY broth (8 g Bactotryptone, 5 g Yeast extract, 5 g NaCl in 500 ml sterile H$_2$O) aliquots and grown for 6 hours at 37° C. The 2 ml cultures were split into 0.5 ml and 1.5 ml aliquots. The bacteria were centrifuged out of solution in an Eppendorf, (trademark) microfuge and the supernatents were transferred to sterile eppendorf (trademark) tubes. The 0.5 ml aliquots were stored at −20° C. as phage stocks. The 1.5 ml aliquots were used to prepare single stranded DNA following the method in the Amersham International M13 sequencing handbook (see below). These DNA samples were then sequenced using oligonucleotides SEQ ID No 22, SEQ ID No 23 and M13 Universal sequencing primer. The reactions were carried out using the Sequenase kit (trademark) according to the manufacturers instructions. All 4 clones had the correct DNA sequence for [Ser$^{17,27}$]G-CSF.

Large-scale single stranded DNA preparation

For single stranded DNA preparations of between 200–500 μg of DNA/ml, the method in the Amersham International "Oligonucleotide Directed Mutagenesis" was used. A detailed procedure is carried out as follows:

LARGE - SCALE SINGLE STRANDED DNA PREP:

A. Preparation of 1 ml phage stock

1. Pick a single TG1 *E.coli* colony from a glucose/minimal medium plate. Grow overnight in 10 ml 2× TY medium, shaken at 37° C. Add 10 μl to 20 ml of fresh medium, and shake at 37° C. for 3 hours.

2. Inoculate 1 ml 2× TY medium in a 10 ml sterile culture tube with 100 μl of 3 hour culture from step 1.

3. Inoculate the 1 ml culture with a recombinant plaque.

4. Incubate for 4 hours with shaking at 37° C. Transfer to a microcentrifuge tube.

5. Centrifuge for 5 minutes at ambient temperature. Pour supernatent into a fresh tube.

Store overnight at 4° C. Set up an overnight culture of TG1 *E.coli* for the next stage.

B. Growth of 100 ml phage culture.

1. Inoculate 100 ml 2× TY medium with 1 ml of overnight TG1 culture and shake at 37° C. to an O.D$_{500}$ of 0.3.

2. Add the 1 ml phage supernatent from A5 (above) to the 100 ml culture.

3. Incubate for 5 hours with shaking at 37° C. Transfer to centrifuge tubes.

4. Centrifuge at 5000×g for 30 minutes at 4° C.

5. Transfer supernatant to a clean centrifuge tube. Take care not to carry over any cells (retain bacterial pellet for RF DNA preparation)

6. Add 0.2 volumes of 20% w/v PEG 6000 in 2.5M NaCl to the supernatent. Mix well and then leave to stand for 1 hour at 4° C.

7. Centrifuge at 5000×g for 20 minutes at 4° C. Dscard supernatent.

8. Centrifuge at 5000×g for 5 minutes, and remove all remaining PEG/NaCl with a drawn out Pasteur pipette.

9. Resuspend the viral pellet in 500 μl water (double distilled) and transfer to a microcentrifuge tube (1.5 ml).

10. Centrifuge for 5 minutes in a microcentrifuge to remove any remaining cells. Transfer the supernatent to a fresh microcentrifuge tube.

11. Add 200 μl 20% PEG 12.5M NaCl to the supernatent mix well then leave to stand at ambient temperature for 15 minutes.

12. Centrifuge for 5 minutes, discard supernatent.

13. Centrifuge for 2 minutes. Carefully remove all traces of PEG/NaCl with a drawn out Pasteur pipette.

14. Resuspend the viral pellet in 500 μl double distilled water.

15. Add 200 μl phenol saturated with 10 mM Tris HCl pH8.0, 1 mM EDTA. Vortex briefly.

16. Stand tube for 15 minutes at room temperature.

17. Centrifuge for 3 minutes.

18. Transfer supernatent to fresh tube.

19. Repeat steps 15–18.

20. Add 500 μl chloroform and extract aqueous phase twice.

21. Add 50 μl 3M sodium acetate and 1 ml absolute ethanol. Mix.

22. Place in a dry ice and ethanol bath for 20 minutes.

23. Centrifuge for 15 minutes.

24. Wash each pellet with 1 ml −20° C. ethanol. Pour off.

25. Vacuum dry pellet and raise in 50 μl double distilled water.

This procedure yields 100–200μg single stranded DNA.

e) Fermentation pICI 1080 was transformed into *E. coli* strain MSD 522 and the resultant recombinants purified and maintained on glycerol stocks at −80° C.

An aliquot of the culture was removed from stock and streaked onto agar plates of L-ampicillin to separate single colonies after overnight growth at 37° C. A single desired colony was removed and resuspended in 10 ml L-ampicillin broth and 100 μl immediately inoculated into each of 10 250 ml Erlenmeyer flasks containing 75 ml L-ampicillin broth. After growth for 16 h at 37° C. on a reciprocating shaker the contents of the flasks were pooled and used to inoculate a fermenter containing 20 L LCM50 growth medium.

Composition of LCM50

| | Made up of distilled water, g/l |
|---|---|
| KH$_2$PO$_4$ | 3.0 |
| Na$_2$HPO$_4$ | 6.0 |
| NaCl | 0.5 |
| Casein hydrolysate (Oxoid L41) | 2.0 |
| (NH$_4$)$_2$SO$_4$ | 10.00 |
| Yeast Extract (Difco) | 10.00 |
| Glycerol | 35.00 |
| L-Leucine | 2.5 |
| L-Threonine | 0.9 |
| MgSO$_4$.7H$_2$O | 0.5 |
| CaCl$_2$.2H$_2$O | 0.03 |
| Thiamine | 0.008 |
| FeSO$_4$/Citric Acid | 0.94/0.02 |
| Trace element Solution (TES) | 0.5 ml |

Fermentations were then carried out at a temperature of 37° C. and pH, controlled by automatic addition of 6M sodium hydroxide solution, of pH 6.7. The dissolved oxygen tension (dOT) set point was 50% air-saturation and was initially controlled by automatic adjustment of the fermenter stirrer speed. Air flow to the fermenter, initially 20 L/min, corresponding to 1 volume per volume per minute (VVM) was increased to 50 L/min (2.5 VVM) when the fermenter stirrer speed approached 80–90% of its maximum. Since the oxygen transfer rate (OTR) of the fermenters was unable to meet the oxygen uptake rate (OUR) of the bacteria at a cell density greater than that corresponding to an OD$_{550}$ of 50 under the conditions described, dOT in the fermenter at cell densities greater than this was maintained at 50% air-saturation by restricting bacteria oxygen uptake rate. This was achieved by formulating the medium to become carbon-limited at OD$_{550}$ of 50 and then supplying a feed of the limiting carbon source, together with ammonium sulphate and yeast extract, at a rate which restricted bacterial growth rate.

Fermentations were performed for 16h and during that time samples were taken for measurement of optical density (OD$_{550}$), cell dry weight and accumulation of G-CSF within the cells. G-CSF accumulation was measured by scanning Coomassie blue stained SDS-PAGE gels of whole cell lysates of the sampled bacteria as is well known in the art.

When OD$_{550}$ reached 25, casein hydrolysate solution (100 g/l Oxzoid L41) was pumped into the fermenters at a rate of 1.5 g/l/h.

When OD$_{550}$ reached approximately 50, the supply of carbon-source in the fermentation batch became exhausted leading to a rapid rise in dOT from 50% air saturation. At this point, a feed containing glycerol (470 g/l), yeast extract (118 g/l) and ammonium sulphate (118 g/l) was pumped into the fermenters at a rate which returned and then maintained the dOT at 50% air saturation with the fermenter stirred at ca 80% of its maximum. After ca 13–14 h this fed-batch feed was replaced with a second feed containing glycerol (715 g/L) and ammonium sulphate (143 g/L) only. Casein hydrolysate feeding was maintained at 1.5 g/L/h throughout. After approximately 16 hours, when microscopic examination of the culture showed the presence of large inclusion bodies within a majority of the cells, bacteria were harvested on a Sorval RC3B centrifuge (7000 g, 30 min., 4° C.) and stored frozen at minus 80° C.

f) Purification

Frozen cell paste (500 g) was resuspended at 4° C. in 50 mM Tris HCl, 25 mM EDTA, pH8.0 (5 litres) using a Silverson model AXR homogeniser. The suspension was lysed by passing three times through a Manton-Gaulin homogeniser at 6000 psi and centrifuged at 5000×g for 30 minutes in a Sorvall RC3C centrifuge using a H6000A rotor. The supernatant was discarded and the pellet fraction stored at −20° C. before further purification.

The pellet fraction (60–100 g) was thawed and resuspended in 1% w/v deoxycholic acid (sodium salt) in 5 mM EDTA, 5 mM dithiothreitol, 50 mM Tris HCl, pH9.0 (1200 ml) containing 1 mg/ml of sodium azide using a Polytron homogeniser with a PTA 20 probe at speed setting 5. The suspension was mixed for 30 minutes at room temperature and centrifuged at 6500×g for 30 minutes in a Sorvall RC 5C centrfigure using a GSA rotor. The supernatant was discarded and the pellet was retreated twice in the same manner. The pellet was next twice resuspended in water (1 litre) and centrifuged at 15,000×g for 20 minutes. The final pellet containing washed inclusion bodies was solubilised in 2% w/v N-lauroyl sarcosine sodium salt (Sarkosyl) in 50 mM Tris. HCl, pH 8.0 (150 ml) containing 1 mg/ml sodium azide. Cuptic sulphate was added to 20 $\mu$M and the mixture stirred for 16 hours at 20° C. before centrifugation at 30,000×g for 30 minutes in a Sorvall RC5C centrifuge using a SS34 rotor. The supernatant containing the derivative was stored at −20° C. in 50 ml aliquots before further purification.

Solubilised derivative (20 ml) was thawed and passed through a 5 $\mu$m filter to remove any particulate material. The filtrate was applied to a column (5×90 cm) of Ultrogel AcA54 equilibrated with 0.3% w/v N-lauroyl sarcosine (sodium salt) in 50 mM Tris. HCl, pH 8.0 containing 1 mg/ml sodium azide at 4° C. The column was eluted with the same buffer at a flow rate of 2.5 ml/minute and fractions of 10 ml were collected. Fractions containing the derivative protein were pooled (approximately 100 ml) and stored at 4° C.

Pooled derivative-containing fractions from several columns were combined (300–500 ml) and dialysed against 10 mM sodium phosphate, 150 mM sodium chloride pH 7.4 (3–5 litres) containing 1 mg/ml sodium azide using an Amicon CH2A-1S spiral cartridge diafiltration apparatus equipped with a S1Y10 membrane (10 kD cut-off). The retentate was centrifuged at 30,000×g for 30 minutes in a Sorvall RC5C centrifuge using an SS34 rotor, and the supernatant dialysed in Spectropor 6–8 kD cut-off dialysis tubing for 40 hours against three changes (8 litres/300 ml of supernatant) of 20 mM sodium acetate, 100 mM sodium chloride, pH 5.4 containing 1 mg/ml sodium azide. The precipitate which formed was removed by centrifugation at 30,000×g for 30 minutes and the supernatant dialysed for 24 hours against water containing 1 mg/ml sodium azide followed by 72 hours against six changes of water. The final retentate was clarified by centrifugation at 30,000×g for 30 minutes and stored frozen at −20° C. (protein concentration about 1 mg/ml) or at 4° C. after freeze drying.

The concentration of N-lauroyl sarcosine (sodium salt) had fallen to below 0.001% w/v after diafiltration and was below the limit of detection (about 0.0001%) of the rpHPLC method used after dialysis against water.

EXAMPLE 2

Preparation of [Ser$^{17,27}$] human G-CSF

The procedure described in Example 1 was repeated except as follows:

The duplex I was phosphorylated with T4 polynucleotide kinase and digested with MstII (10 units) in 1×H buffer (BCL; 30 $\mu$l) for 2 hours at 37° C.

Following precipitation with ethanol, the 143 bp EcoRI-MstII fragment was purified on a 10% polyacrylamide gel containing 7M urea, isolated by electroelution from a gel slice and the DNA strands annealed as described in Reference Example 1.

The synthetic EcoRI-MstII fragment described above was cloned into the plasmid vector pAG88 described in Reference Example 1. For vector preparation, pAG88 (10$\mu$g) was digested with MstII (20 units; BCL) in 1×H buffer (BCL; 100 $\mu$l) for 2 hours at 37° C. The DNA was precipitated with ethanol from 0.3M sodium acetate at −20° C. then digested with EcoRI (20 units; BCL) in 1×H buffer (BCL; 100 $\mu$l) for 2 hours at 37° C. Following precipitation with ethanol, the large EcoRI-MstII fragment was purified on a 1% agarose gel and purified using Geneclean (trademark) as described by the manufacturer (Bio 101, USA). Colonies containing the synthetic fragment were confirmed by screening with a radioactive probe prepared from oligonucleotide (SEQ 1D No 24) and the correct sequence confirmed by DNA sequencing as described in Reference Example 1. The plasmid containing the gene for [Ser$^{17,27}$]G-CSF was designated pICI1107. The gene was cloned into expression vector pICI0020 and fermentation and protein purification was effected as described in Example 1.

EXAMPLE 3

Preparation of [Arg$^{11}$Ser$^{17,27,60,65}$]human G-CSF

The procedure described in Reference Example 2 was repeated using the mutagenic template M13mp18 containing the gene for [Ser$^{17,27}$]G-CSF described in Example 1 or 2. The mutagenic oligonucleotides used are designated SEQ 1D No 28 and SEQ 1D No 29 (as hereinafter defined).

The triplet ACG in SEQ 1D No 28 serves to convert Gln at position 11 to Arg and the first and last AGA triplets in SEQ ID No 29 serve to convert Pro at positions 65 and 60 to Ser. The mutagenesis was carried out as described in Reference Example 2 using SEQ ID No 29 in a single priming mutagenesis. This yielded a single plaque which incorporated the Pro 60 Ser and Pro 65 Ser changes. Single stranded DNA was prepared from this plaque as described in Reference Example 2. This DNA was used as a mutagenic template in a single priming mutagenesis using SEQ ID No 28 as mutagenic primer. This yielded >100 plaques, 3 of which were screened by DNA sequencing as previously described. All 3 had the full set of changes incorporated. Double-stranded RF DNA was prepared from one of the plaques by following the procedure for large scale preparation of single stranded DNA (step d in Example 1) to step B5. The RF DNA was extracted from the bacterial pellet by the alkali lysis procedure of Birnboim and Doly (Nucleic Acids Research (1979) 7, 1513–1523) and purified by caesium chloride density gradient centrifugation as described in "Molecular Cloning—a Laboratory Manual" by Sambrook, Fritsch and Maniatis (Cold Spring Harbor Publication). The purified RF DNA was digested with EcoRI and SalI in buffer H as described previously and the small fragment, containing the trp promoter, ribosome binding site, translation initiation codon and gene for [Arg$^{11}$,Ser$^{17,27,60,65}$]G-CSF isolated from a 0.7% agarose gel by use of Geneclean (TM). The fragment was ligated into an EcoRI-SalI digested pICI0020 vector, using a 2:1 molar excess of insert to vector, with T4 DNA ligase (BRL) and ligase buffer, essentially as described previously. The ligation mix was used to transform *E.Coli* strain HB101. Transformants were selected for by growth on L-agar plates containing 50 μg/ml ampicillin. Colonies were screened for the presence of the inserted DNA by restriction analysis of plasmid DNA prepared by the method of Birnboim and Doly as described in "Molecular Cloning—a Laboratory Manual" Sambrook, Fritsch and Maniatis (Cold Spring Harbor Publication). Plasmid DNA from a colony containing the expected 619 bp EcoRI - SalI insert was used to transform *E.coli* strain MSD522 and designated pICI1239. Fermentation and purification were effected as described in Example 1.

EXAMPLE 4

Preparation of [Ser$^{17,27,115,116}$Glu$^{111}$]human G-CSF

The procedure described in Example 3 was repeated using the mutagenic template M13mp18 containing the gene for [Ser$^{17,27}$]G-CSF described in Example 1 or 2. The mutagenic oligonucleotide used is designated SEQ ID No 30 (as hereinafter defined)

The triplet GCT serves to convert Thr at position 116 to Ser, the triplet AGA serves to convert Thr at position 115 to Ser and the triplet TTC serves to convert Ala at position 111 to Glu. The mutagenesis procedure was essentially as described for Example 3 and the expression cassette was transferred to the expression plasmid to give pICI 1243. Fermentation and purification was effected as described in Example 1.

EXAMPLE 5

Preparation of [Arg$^{11}$, Ser$^{17,27}$, Lys$^{58}$, Ar$^{165}$] human G-CSF

The procedure described in Example 3 was repeated using the mutagenic template M13mp18 containing the gene for [Ser$^{17,27}$]G-CSF described in Example 1 or 2. The mutagenic oligonucleotides used are designated SEQ ID No 28, SEQ ID No 31 and SEQ ID No 32 (as hereinafter defined)

The triplet TTT in SEQ ID No 31 serves to convert Trp at position 58 to Lys and in SEQ ID No 32 the second GCG triplet serves to convert Tyr at position 165 to Arg.

The mutagenesis procedure was initially carried out as a double priming experiment using SEQ ID No 31 and SEQ ID No 32 as mutagenic oligonucleotides as described for Reference Example 2. This yielded 2 plaques both of which had the SEQ ID No 32 change (Tyr 165 Arg) but not the SEQ ID No 31 change. Single stranded DNA was prepared from one of these plaques as described in Example 1. This DNA was used as a mutagenic template in a double priming mutagenesis using SEQ ID No 28 and SEQ ID No 31 as mutagenic primers. This yielded 2 plaques one of which had the complete set of changes incorporated and the expression cassette was transferred to the expression plasmid to give pICI 1246. Fermentation and purification was effected as described in Example 1.

EXAMPLE 6

Preparation of [Glu$^{15}$,Ser$^{17,27}$,Ala$^{26,28}$,Lys$^{30}$] human G-CSF a) The procedure described in Example 3 was repeated using the mutagenic template M13mp18 containing the gene for [Ser$^{17,27}$]G-CSF described in Example 1 or 2. The mutagenic oligonucleotides used are designated SEQ ID No 33 and SEQ ID No 34 (as hereinafter defined).

The triplet TTC in SEQ ID No 33 serves to convert Leu at position 15 to Glu. In SEQ ID No 34 the first TTT triplet serves to convert Ala at position 30 to Lys and the triplets AGC serve to convert Gly at position 28 and 26 to Ala.

The mutagenesis procedure was essentially as described in Reference Example 2 as a double priming experiment and the expression cassette transferred to the expression plasmid to give pICI 1266. Fermentation was effected as described in Example 1.

b) Purification

Frozen cell paste was lysed and the crude pellet fraction separated as in Example 1. The inclusion bodies in the pellet containing this protein were solubilised by the deoxycholic acid (sodium salt) buffer described in Example 1. The following modified procedure was used for this protein.

Crude pellet fraction (60-100 g) was thawed and resuspended in 25 mM EDTA, 50 mM Tris.HCl, pH 8.0 (1200 ml) using a Polytron homogeniser with a PTA 20 probe at speed setting 5. The suspension was mixed at room temperature for 30 minutes and centrifuged at 6,500×g for 30 minutes in a Sorvall RC5C centrifuge using a GSA rotor. The supernatant was discarded and the pellet retreated twice in the same manner. The pellet was next twice resuspended in water (1 litre) and centrifuged as in Example 1. Thereafter the purification procedure was as in Example 1.

EXAMPLE 7

Preparation of [Ser$^{17,27}$Lys$^{49,58}$ Ala$^{44,51,55}$] human G-CSF

The procedure described in Example 3 was repeated using the mutagenic template M13mp18 containing the gene for [Ser$^{17,27}$]G-CSF described in Example 1 or 2. The mutagenic oligonucleotides used are designated SEQ ID No 35 and SEQ ID No 36 (as hereinafter defined). In SEQ ID No 35 the triplets AGC serve to convert Gly to Ala at position 51 and Pro to Ala at position 44 and the triplet TTT serves to convert Leu to Lys at position 49. In SEQ ID No 36 the triplet TTT serves to convert Trp to Lys at position 58 and the second AGC triplet serves to convert Gly to Aln at position 55.

The mutagenesis was carried out as a double priming experiment as described in Reference Example 2. This yielded 16 plaques. 8 Plaques were screened by DNA sequencing as described in Example 3. All plaques had the SEQ ID No 36 changes (Gly55Ala, Trp58Lys) but none had the SEQ ID No 35 changes. Single stranded DNA was prepared from one of these plaques as described in Example 1(*d*) and used as a mutagenic template in a single priming mutagenesis using SEQ ID No 35 as mutagenic primer. This yielded 50 plaques, 3 of which were screened by DNA sequencing, 2 had the complete set of changes. The expression cassette was transferred to the expression plasmid to give pICI 1297. Fermentation and purification was effected as described in Example 1.

EXAMPLE 8

Preparation of [Arg$^{11}$,Glu$^{15}$,Ser$^{17,27,60,65}$, Lys$^{30}$] human G-CSF The procedure described in Example 3 was repeated using the mutagenic template M13mp18 containing the gene for [Glu$^{15}$,Ser$^{17,27}$,Ala$^{26,28}$, Lys$^{30}$] human G-CSF described in Example 6. The mutagenic oligonucleotide used is designated SEQ ID No 28 which serves to convert Gln at position 11 to Arg. The modified gene was isolated and ligated into pICI0020 vector (Example 1). This vector was used to transform E. coli strain MSD522 as described in Example 3 and designated pICI1347. pICI1347 plasmid DNA was isolated from MSD522, purified by caesium chloride density centrifugation and digested to completion with BamHI and SalI (BCL) Plasmid DNA (5 μg) was incubated at 37° C. for 2 hours in BCL high salt buffer (100 μl) (50 mM tris HCl pH 7.5, 10 mM MgCl$_2$, 100 mM NaCl, 1 mM dithioerythritol) containing BamHI (40 units) and SalI (50 units). The DNA was precipitated by addition of 3M sodium acetate (10 μl) and absolute ethanol (250 μl) and cooling to −20° C. for 2 hours, collected by centrifugation (10 min at 10,000 rpm), dried in vacuo and dissolved in water (10 μl). Sample loading buffer (2 μl containing 240 mM tris acetate pH 7.8, 6 mM EDTA, 20% sucrose, 0.2% xylene cyanol and 0.2% bromophenol blue) was added and the mixture loaded onto a 0.7% agarose preparative gel (in 40 mM tris acetate (pH 7.8) and 1 mM EDTA) containing ethidium bromide (0.5 μg/ml) and electrophoresed at 100 volts for 1 hour. The large BamHI - SalI vector fragment was isolated from a 0.7% agarose gel by use of Geneclean (trademark). In a similar manner, pICI1239 plasmid DNA from Example 3 was isolated and digested with BamHI and SalI. The small BamHI - SalI fragment, containing the Ser codons at position 60 and 65, was isolated and ligated to the large BamI - SalI vector fragment described above. The mixture was used to transform E. coli strain MSD522 and the plasmid designated pICI1348. Fermentation and purification was effected as described in Example 6.

EXAMPLE 9

The procedure of Examples 1 and 2 was repeated using E.coli strain TG1 instead of E.coli strain MSD 522 in the fermentation step (see for example Example 1(e)).

EXAMPLE 10

Alternative Extraction Process for Human [Met$^{-1}$, Arg$^{11}$, Ser$^{17,27,60,65}$]G-CSF Frozen cell paste (640 g) was resuspended at 4° C. in 50 mM Tris HCl, 5 mM EDTA, 5 mM dithiothreitol, 2M urea, pH 8.0 containing 1 mg/ml sodium azide (5 litres) using a Polytron homogeniser with a PTA20 probe at speed setting 7/8. The suspension was lysed by passing three times through a Manton-Gaulin Lab 60/60 homogeniser at 6000 psi and flushed through with a further 1 litre of buffer. Cooling was provided by a single pass Conair chiller at −20° C. The lysate was centrifuged at 5000 ×g for 30 minutes in a Sorvall RC3C centrifuge using an H6000A rotor.

The supernatant was discarded and the pellet (about 450 g) was resuspended in the same buffer (10 litres). The suspension was mixed for 30 minutes at room temperature and centrifuged at 5000 rpm for 30 minutes in two Sorvall RC3C centrifuges using H6000A rotors. the supernatant was discarded and the pellet retreated twice in the same manner. The pellet was next twice resuspended in water (10 litres) and centrifuged at 5000 rpm for 30 minutes. The final pellets containing washed inclusion bodies were resuspended in 2% w/v N-lauroyl sarcosine sodium salt in 50 mM Tris HCl, pH 8.0 (1 litre) containing 1 mg/ml sodium azide using a Polytron homogeniser at speed setting 7. 20 mM cuptic sulphate in water (1.5 ml) was added and the mixture stirred overnight at room temperature before centrifugation at 10,000 rpm for 30 minutes in a Sorvall RC5C centrifuge using a GSA rotor.

The supernatant containing the derivative was filtered through a 5 μm filter to remove any particulate matter, diluted six-fold with 50 mM Tris HCl, pH 8.0 containing 1 mg/ml sodium azide at 4° C., and diafiltered at maximum pressure in an Amicon DC20 ultrafiltration device fitted with a S10Y10 cartridge (10 kd cut-off) against 10 mM sodium phosphate, 150 mM sodium chloride pH 7.4 (90 litres) containing 1 mg/ml sodium azide. A precipitate formed towards the end of the diafiltration.

The retentate (2.1 mg/ml total protein, 1.7 mg/ml product) was collected in 4 litre, screw top, polypropylene containers and incubated overnight at 37° C. The precipitate which formed was removed by centrifugation at 5000 rpm for 45 minutes in a Sorvall RC3C, and the supernatant stored at 4° C.

Monitoring by SDS-PAGE and rpHPLC, showed that during the final heat treatment contaminating E. coli proteins, product oligomers, and degradation products were selectively precipitated, with some 85% of the desired product remaining in solution. The highly enriched clarified, heat treated product solution was fully biologically active and stable at 20 mg/ml at 37° C. over two weeks with no evidence of proteolytic degradation and less than 20% precipitation. This provided an excellent intermediate for further chromatographic purification.

EXAMPLE 11

Characterization of G-CSF and derivatives thereof

A water solution of [Met$^{-1}$,Ser$^{17}$] G-CSF and derivatives thereof (Examples 1–9) (protein concentration about 1 mg/ml) were concentrated to at least 11 mg/ml of protein on an Amicon YM10 membrane at 4° C. To prevent any precipitation during concentration, the starting solution pH5.5 was first adjusted to pH8.5 by the addition of ammonium hydroxide to a final concentration of about 0.25 mM. After concentration the pH of the solution had fallen to about 8.0.

The concentrated protein solution was adjusted to 10 mg/ml protein (estimated from a 1 mg/ml solution giving an A280 of 1.0) by addition of 20 fold concentrated phosphate buffered saline. This 10 mg/ml solution of derivative in 10 mM sodium phosphate, 150 mM sodium chloride, pH7.4 (PBS) provided a common stock solution from which to establish homogeneity, identity, biological activity and solution stability of the protein.

A stock solution of human G-CSF at 1 mg/ml concentration in PBS prepared as described in Reference Example 1 was also prepared.

Each protein was shown to be at least 95% one component by PAGE-SDS run under reducing and non-reducing conditions and by reverse phase HPLC. Repeated amino acid composition analysis after acid hydrolysis in 6NHCl at 110° C. provided amino acid ratios for each derivative, and an accurate measurement of the protein concentration in the stock solution. This protein concentration together with the mean of bioassay titres obtained on at least six different days was used to determine the specific activity of the derivative. N-terminal sequence analysis and electrospray mass spectrometric analysis of selected derivatives gave the expected sequences and molecular weights.

EXAMPLE 12

Preparation of [Arg[11],Ser[17,27,60,65]] human G-CSF using production vector including trp promoter a) Plasmid pICI1239 (described in Example 3) was digested with EcoRI and SalI in buffer H as described previously. The small EcoRI-SalI fragment containing the trp promoter, ribosome binding site and gene for [Arg[11],Ser[17,27,60,65]]hu G-CSF was isolated from a 0.7% agarose gel by use of Geneclean(TM). A vector fragment was prepared from pICI 0080 (see Reference Example 6) by digestion with EcoRI and XhoI in buffer H and the large EcoRI-XhoI fragment isolated from a 0.7% agarose gel by use of Geneclean(TM). The small EcoRI-SalI fragment was ligated into the EcoRI-XhoI vector fragment, using a 2:1 molar excess of insert to vector as described previously and the ligation mix used to transform $E.\ coli$ strain MSD 522. Transformants were selected for growth on L-agar plates containing tetracycline (15 μg/ml). Three colonies were selected and grown up in M9 minimal media (75 ml) containing supplements and tetracycline (15 μg/ml) at 37° C. for 20 hours on a reciprocating shaker. Protein accumulation was measured by scanning Coomassie blue stained SDS-PAGE gels of whole cell lysate. All three clones expressed [Arg[11],Ser[17,27,60,65]]hu G-CSF. Plasmid DNA from one of the colonies was designated pICI1327 and the sequence of the promoter and gene confirmed by standard dideoxy sequencing procedures as described previously.

b) Fermentation pICI 1327 was transformed into $E.\ coli$ strain MSD 522 and the resultant recombinants purified and maintained on glycerol stocks at −80° C.

An aliquot of the culture was removed from stock and streaked onto agar plates of tetracycline to separate single colonies after overnight growth at 37° C. A single desired colony was removed and resuspended in 10 ml tetracycline broth and 100 μl immediately inoculated into each of 3 250 ml Erlenmeyer flasks containing 75 ml tetracycline broth. After growth for 16 h at 37° C. on a reciprocating shaker the contents of the flasks were pooled and used to inoculate a fermenter containing 20 L growth medium.

Composition of Growth Medium

| | Made up of distilled water g/l |
|---|---|
| KH$_2$PO$_4$ | 3.0 |
| Na$_2$HPO$_4$ | 6.0 |
| NaCl | 0.5 |
| Casein hydrolysate (Oxoid L41) | 2.0 |
| (NH$_4$)$_2$SO$_4$ | 10.00 |
| Yeast Extract (Difco) | 10.00 |
| Glycerol | 35.00 |
| L-Leucine | 0.625 |
| MgSO$_4$.7H$_2$O | 0.5 |
| CaCl$_2$.2H$_2$O | 0.03 |
| Thiamine | 0.008 |
| FeSO$_4$/Citric Acid | 0.04/0.02 |
| Trace element Solution (TES) | 0.5 ml l$^{-1}$ |
| Tetracycline | 10 mg l$^{-1}$ |

Fermentations were then carried out at a temperature of 37° C., and at a pH, controlled by automatic addition of 6M sodium hydroxide solution, of pH 6.7. The dissolved oxygen tension (dOT) set point was 50% air-saturation and was initially controlled by automatic adjustment of the fermenter stirrer speed. Air flow to the fermenter, initially 20 L/min, corresponding to 1 volume per volume per minute (VVM) was increased to 50 L/min (2.5 VVM) when the fermenter stirrer speed approached 80–90% of its maximum. Since the oxygen transfer rate (OTR) of the fermenters was unable to meet the oxygen uptake rate (OUR) of the bacteria at a cell density greater than that corresponding to an OD$_{550}$ of 50 under the conditions described, dOT in the fermenter at cell densities greater than this was maintained at 50% air-saturation by restricting bacteria oxygen uptake rate. This was achieved by formulating the medium to become carbon-limited at OD$_{550}$ of 50 and then supplying a feed of the limiting carbon source, together with ammonium sulphate and yeast extract, at a rate which restricted bacterial growth rate.

Fermentations were performed for 18 h and during that time samples were taken for measurement of optical density (OD$_{550}$), cell dry weight and accumulation of [Arg[11], Ser[17,27,60,65]]human G-CSF within the cells. [Arg[11],Ser[17,27,60,65]]human G-CSF accumulation was measured by scanning Coomassie blue stained SDS-PAGE gels of whole cell lysates of the sampled bacteria as is well known in the art.

When OD$_{550}$ reached 35 (8.5h), casein hydrolysate solution (100 g/l Oxzoid L41) was pumped into the fermenters at a rate of 0.75 g/l/h. When OD$_{550}$ reached approximately 50, the supply of carbon-source in the fermentation batch became exhausted leading to a rapid rise in dOT from 50% air saturation. At this point, a feed containing glycerol (470 g/l), yeast extract (118 g/l) and ammonium sulphate (118 g/l) was pumped into the fermenters at a rate which returned and then maintained the dOT at 50% air saturation with the fermenter stirrer at ca 70–80% of its maximum. Casein hydrolysate feeding was maintained at 0.75 g/l/h throughout. After approximately 18 hours, when microscopic examination of the culture showed the presence of large inclusion bodies within a majority of the cells, bacteria were harvested on a Sorval RC3B centrifuge (7000 g, 30 min., 4° C.) and stored frozen at minus 80° C.

c) Purification

Purification was effected as described in Example 1(f)

EXAMPLE 13

Preparation of [Arg[11],Ser[17,27,60,65]]human G-CSF using production vector including T7A3 promoter a) An EcoRI-SalI fragment, containing a T7A3 promoter, a trp leader ribosome binding site sequence and a gene for [Ser[17,27]]hu G-CSF was sub-cloned into M13 mp18 as described in part d) of Example 1. The sequence of the EcoRI-SalI fragment is set out in SEQ ID No 50 and FIG. 3, SEQ ID No 50 consists of the EcoRI restriction site (nucleotides 1–6), the A3 promoter sequence of bacteriophage T7 (nucleotide 7–52), the trp leader ribosome binding site sequence (nucleotides 53–78)and translation initiation codon (nucleotides 79–81). FIG. 3 sets out the nucleotide sequence of [Ser[17,27]]human G-CSF terminating in the SalI restriction site. It will be appreciated that the 3' terminal ATG codon of SEQ ID No 50 immediately precedes the ACT codon which codes for threonine (amino acid 1) in FIG. 3. The 5' nucleotide sequence AATTCAGT is thus absent from the EcoRI-SalI fragment. The EcoRI-SalI fragment may also be prepared by excision from pICI 1295 (see Reference Example 7). Site-directed mutagenesis was performed on single-stranded DNA as described in Reference Example 2 using oligonucleotide SEQ ID No 28 to convert the codon for Gln at position 11 to Arg. Double-stranded RF DNA was prepared from a plaque containing the Gln[11]→Arg[11] change as described in Example 3, except that at step B3 incubation was for 3 hours instead of 5 hours, and digested with EcoRI (as described previously) and SnaBI (as described in Reference Example 5). The resulting 144 bp EcoRI-SnaBI fragment containing the T7A3 promoter, trp leader ribosome binding site sequence and gene fragment with Arg[11] codon was isolated and ligated to an EcoRI-SnaBI cut vector from pICI 1327 (which contains codons for Ser[60] and Ser[65] and is described in Example 12). The ligation mix was used to transform E.coli strain MSD522 and transformants selected for growth on L-agar plates containing tetracycline (15 μg/mg). Plasmid DNA from a colony containing the expected T7A3 promoter and [Arg[11], Ser[17,27,60,65]] hu G-CSF gene sequence were identified by sequencing DNA from the isolated plasmid and designated pICI 1386.

The fermentation was effected according to two alternative processes (b) and (c) below. Process (b) was effected at 37° C. and after 16 hours fermentation as described, microbial biomass was 35 g/l and [Arg[11], Ser[17,27,60,65]]human G-CSF was estimated to be accumulated to 7 g/l fermentation broth. Process (c) was effected at 30° C. and the fermentation was accordingly slower because of the lower fermentation temperature. With regard to process(c), after 35 hours, the microbial biomass was 55 g/l and the [Arg[11],Ser[17,27,60,65]]human G-CSF yield was estimated to be accumulated to 15 g/l fermentation broth.

b) E.Coli strain CGSC 6300 (genotype F−,λ−, lac+) obtained from the E.coli Genetic Stock Centre was transformed with plasmid pICI 1386. The resultant strain CGSC 6300 (pICI 1386) was purified and maintained in glycerol stocks at −80° C. An aliquot of the culture was removed from stock and streaked onto agar plates of L-tetracycline to separate single colonies after overnight growth (16 h) at 37° C. A single colony of CGSC 6300 (pICI 1386) was removed and resuspended in 10 ml L-tetracycline broth and 100 μl immediately inoculated into each of twenty 250 ml Erlenmeyer flasks containing 75 ml of L-tetracycline broth. After growth for 16 h at 37° C. on a reciprocating shaker the contents of the flasks were pooled, and used to inoculate a fermenter containing 20 litres of modified LCM50 growth medium. The composition of the growth medium is in Table 1.

TABLE 1

| Composition of growth medium Modified LCM50 Growth Medium (A) | |
|---|---|
| | made up with distilled water g/l |
| KH$_2$PO$_4$ | 3.0 |
| Na$_2$HPO$_4$ | 6.0 |
| NaCl | 0.5 |
| Casein hydrolysate (Oxoid L41) | 2.0 |
| (NH$_4$)$_2$SO$_4$ | 10.0 |
| Yeast Extract (Difco) | 20.0 |
| Glycerol | 35.0 |
| MgSO$_4$.7H$_2$O | 0.5 |
| CaCl$_2$.2H$_2$O | 0.03 |
| Thiamine | 0.008 |
| FeSO$_4$/Citric acid | 0.04/0.02 |
| Trace element Solution (TES) | (0.5 ml l$^{-1}$) |

TABLE 1-continued

| Composition of growth medium Modified LCM50 Growth Medium (A) | |
|---|---|
| | made up with distilled water g/l |
| Tetracycline | (10 mg l$^{-1}$) |

The fermentation was then carried out at a temperature of 37° C. and at a pH, controlled by automatic addition of 6M sodium hydroxide solution, of pH 6.7. The dissolved oxygen tension (dOT) set point was 50% air saturation and was initially controlled by automatic adjustment of the fermenter stirrer speed. Air flow to the fermenter was initially 20 L/min corresponding to 1.0 volume volume per minute (VVM) and was increased to 45 L/min manually when the fermenter stirrer speed reached its maximum (1000 rpm). The fermentation was performed for 16 h and during that time samples were taken for measurement of optical density of the culture (OD$_{550}$ biomass concentration, total microbial protein concentration and accumulation of [Arg[11],Ser[17,27,60,65]]human G-CSF within the bacterial cells. Accummulation was measured by scanning Coomassie blue stained SDS-PAGE gels of whole cell lysates of the sampled bacteria as is well known in the art. Total microbial protein was estimated by the method of Lowry. A solution of yeast extract (225 g/L) was pumped into the fermenter 4.5 h post inoculation at 1.7 g/L/h.

When the supply of carbon source (glycerol) in the growth medium became exhausted dOT increased rapidly from 50% air saturation. At this point a feed containing glycerol (714 g/l) and ammonium sulphate (143 g/L) was pumped. Since the bacterial oxygen sulphate rate (OUR) approached the maximum oxygen transfer rate of the fermenter (OTR) just prior to the carbon source in the batch growth medium becoming exhausted, the feed was pumped into the fermenter at a rate which restricted the bacterial OUR to approximately 80–90% of the fermenters maximum OTR. The feed rate was adjusted manually to return and then maintain dOT at 50% air saturation under the conditions described.

c) The fermentation process described in (b) was repeated but at a temperature of 30° C. for 35 hours. Except for the fermentation temperature of 30° C. the medium and fermentation conditions were identical to those described in (b).

d) Purification was effected as described in Example 1(f).

EXAMPLE 14

Preparation of [Glu[15],Ser[17,27],Ala[26,28],Arg[30]]hu G-CSF

A mutagenic template, M13mp18 containing the gene for [Glu[15],Ser[17,27]Ala[26,28],Lys[30]]hu G-CSF, was prepared as described in part (d) of Example 1 with plasmid pICI 1266 replacing pICI 1080. The procedure described in Example 3 was repeated using the above template with mutagenic oligonucleotide designated SEQ ID No.37. This serves to convert the codon for Lys at position 30 to Arg. Double stranded RF DNA was prepared from one phage containing the desired change. An EcoRI-SalI expresson cassette was isolated and cloned into pICI 0080 as described in Example 12 to give pICI 1343.

EXAMPLE 15

Preparation of [Arg$^{11,23}$,Ser$^{17,27,60,65}$]hu G-CSF

A mutagenic template, M13mp18 containing the gene for [Arg$^{11}$,Ser$^{17,27,60,65}$]hu G-CSF, was prepared as described in part (d) of Example 1 with plasmid pICI 1239 replacing pICI 1080. The procedure described in Example 3 was repeated using the above template with mutagenic oligonucleotide designated SEQ ID No 38. This serves to convert the codon for Lys at position 23 to Arg. Double-stranded RF DNA was prepared from one phage containing the desired change and the expression cassette isolated and cloned as described in Example 14 to give pICI 1388.

Further processing to yield the title compound and the purification of the title compound were effected as described in Example 1.

EXAMPLE 16

Preparation of [Arg$^{11,34}$,Ser$^{17,27,60,65}$]hu G-CSF

The procedure described in Example 15 was repeated with oligonucleotide designated SEQ ID No.38 replaced by SEQ ID No.39 (this serves to convert the codon for Lys at position 34 to Arg) to give pICI 1389.

Further processing to yield the title compound and the purification of the title compound were effected as described in Example 1.

EXAMPLE 17

Preparation of [Arg$^{11,40}$,Ser$^{17,27,60,65}$]hu G-CSF

The procedure described in Example 15 was repeated with oligonucleotide SEQ ID No.38 replaced by SEQ ID No.40 (this serves to convert the codon for Lys at position 40 to Arg) to give pICI 1390.

Further processing to yield the title compound and the purification of the title compound were effected as described in Example 1.

EXAMPLE 18

Preparation of [Ala$^1$,Thr$^3$,Tyr$^4$,Arg$^{5,11}$,Ser$^{17,27,60,65}$]hu G-CSF The procedure described in Example 15 was repeated with oligonucleotide SEQ ID No.38 replaced by SEQ ID No.41 (this serves to convert codons for Thr, Leu, Gly and Pro at positions 1, 3, 4 and 5 to Ala, Thr, Tyr and Arg respectively to give pICI 1391.

The polypeptide of this Example illustrates that the modification of the present invention may be applied to a polypeptide known to possess G-CSF activity in order to improve the solution stability of the polypeptide. The known polypeptide is [Ala$^1$,Thr$^3$,Tyr$^4$,Arg$^5$,Ser$^{17}$]hu G-CSF which is described in European Patent Publication No. 272,703 of Kyowa Hakko Kogyo Co. Ltd.

Further processing to yield the title compound and the purification of the title compound were effected as described in Example 1.

EXAMPLE 19

Preparation of [Arg$^{11}$,Ser$^{17,27}$.]hu G-CSF

The procedure described in Example 4 was repeated with oligonucleotide SEQ ID No.30 replaced by SEQ ID No.28 (this serves to convert the codon for Gln at position 11 to Arg). The expression cassette was transferred to expression plasmid pICI 0080, instead of pICI 0020 as described in Example 14 to give pICI 1405.

Further processing to yield the title compound and the purification of the title compound were effected as described in Example 1.

EXAMPLE 20

Preparation of [Ser$^{17,27,60,65}$]hu G-CSF

The procedure described in Example 19 was repeated with oligonucleotide SEQ ID No.28 replaced by SEQ ID No.29 (this serves to convert the codons for Pro at 60 and 65 to Ser) to give pICI 1400.

Further processing to yield the title compound and the purification of the title compound were effected as described in Example 1.

EXAMPLE 21

Preparation of [Arg$^{11}$,Ser$^{17,27,60}$]hu G-CSF

The procedure described in Example 6 was repeated with oligonucleotides SEQ ID No.33 and SEQ ID No.34 replaced by SEQ ID No.28 and SEQ ID No.42. These serve to convert the codons for Gln at position 11 and Pro at position 60 to Arg and Set respectively. The expression cassette was transferred to the expression plasmid pICI 0080 instead of pICI 0020 to give pICI 1401.

Further processing to yield the title compound and the purification of the title compound were effected as described in Example 1.

EXAMPLE 22

Preparation of [Arg$^{11}$,Ser$^{17,27,65}$]hu G-CSF

The procedure described in Example 3 was repeated with oligonucleotide designated SEQ ID No.29 replaced by SEQ ID No.43 (this serves to convert the codon for Pro at position 65 to Ser) to give pICI 1418.

Further processing to yield the title compound and the purification of the title compound were effected as described in Example 1.

EXAMPLE 23

Preparation of [Ser$^{17,27,60}$]hu G-CSF

The procedure described in Example 19 was repeated with oligonucleotide designated SEQ ID No.28 replaced by SEQ ID No.42 (this serves to convert the codon for Pro at position 60 to Ser) to give pICI 1402.

Further processing to yield the title compound and the purification of the title compound were effected as described in Example 1.

EXAMPLE 24

Preparation of [Ser$^{17,27,65}$]hu G-CSF

The procedure described in Example 4 was repeated with oligonucleotide designated SEQ ID No.30 replaced by SEQ ID No.43 (this serves to convert the codon for Pro at position 65 to Ser) to give pICI 1420.

Further processing to yield the title compound and the purification of the title compound were effected as described in Example 1.

EXAMPLE 25

Preparation of
[Arg$^{11}$,Glu$^{15,111}$,Ser$^{17,27,60,65,115,116}$,Ala$^{26,28}$,Lys$^{30}$]hu G-CSF Plasmid pICI 1348, described in Example 8, was digested with XbaI in buffer M and then with SalI in buffer H and the large XbaI-SalI vector fragment isolated from a 0.7% agarose gel as described previously. Plasmid pICI 1243, described in Example 4, was digested with XbaI and SalI as described above and the small XbaI-SalI fragment isolated from a 0.7% agarose gel and ligated to the XbaI-SalI vector fragment above. The ligation mix was used to transform E.coli strain MSD 522 and transformants selected for growth on L-agar plates containing ampicillin (50 µg/ml). Three colonies were screened for expression of protein as described in Example 12 but replacing tetracycline by ampicillin at 50 µg/ml. Plasmid DNA from a colony expressing the correct protein was designated pICI 1421.

Further processing to yield the title compound was effected as described in Example 3 and purification was effected as described in Example 6.

EXAMPLE 26

Preparation of [Arg$^{11,165}$,Glu$^{15,27,60,65}$,Glu$^{26,28,30,58}$]hu G-CSF

A mutagenic template, M13mp18 containing the gene for [Arg$^{11}$,Glu$^{15}$, Ser$^{17,27,60,65}$,Ala$^{26,28}$,Lys$^{30}$]hu G-CSF, was prepared as described in part (d) of Example 1 with plasmid pICI 1348 (described in Example 8) replacing pICI 1080. The procedure described in Example 3 was repeated using the above template with mutagenic oligonucleotides designated SEQ ID No.28 and SEQ ID No.29 replaced by SEQ ID No.44 and SEQ ID No.32 (these serve to convert the codons for Trp at position 53 to Lys and Tyr at position 165 to Arg) to give pICI 1422.

Further processing to yield the title compound was effected as described in Example 3 and purification was effected as described in Example 6.

EXAMPLE 27

Preparation of
[Arg$^{11}$,Glu$^{15}$,Ser$^{17,27,60,65}$,Ala$^{26,28,44,51,55}$, Lys$^{30,49,58}$]hu G-CSF A mutagenic template was prepared as described in Example 26. The procedure described in Example 4 was repeated using the above template with mutagenic oligonucleotide designated SEQ ID No.30 replaced by SEQ ID No.45 (this serves to convert the codons for Pro at position 44, Leu at position 49 and Gly at positions 51 and 55 to Ala, Lys, Ala and Ala respectively) to give pICI 1423.

Further processing to yield the title compound was effected as described in Example 3 and purification was effected as described in Example 6.

EXAMPLE 28

Preparation of [Arg$^{11,165}$,Glu$^{15,111}$,Ser$^{17,27,60,65,115,116}$, Ala$^{26,28,44,51,55}$,Lys$^{30,49,58}$]hu G-CSF A mutagenic template was prepared as described in part (d) of Example 1 with pICI 1080 replaced by pICI 1423, described in Example 27. The procedure described in Example 3 was repeated using the above template and oligonucleotides designated SEQ ID No.28 and SEQ ID No.29 replaced by SEQ ID No.32 and SEQ ID No.30 to give pICI 1424.

Further processing to yield the title compound was effected as described in Example 3 and purification was effected as described in Example 6.

REFERENCE EXAMPLE 1

Preparation of human G-CSF a) Preparation of a synthetic gene for human G-CSF

A DNA sequence (FIG. 2) encoding the amino-acid sequence of the polypeptide of FIG. 2 (human G-CSF) was designed according to the following considerations:

1) Single—stranded cohesive termini to allow ligation at suitable sites in a plasmid.
2) A series of restriction endonuclease sequences throughout the gene to facilitate subsequent genetic manipulation.
3) Translation termination codon.
4) Codons at the 5'-end of the coding region were normally chosen to be A/T rich. Other codons were normally chosen as those preferred for expression in E.coli.

The gene was assembled from the 18 oligonucleotides designated SEQ ID No.1 - SEQ ID No.18 and shown hereinafter.

Preparation of Oligonucleotides

The oligonucleotide sequences shown hereinafter were prepared on an Applied Biosystems 380A DNA synthesiser from 5'-dimethoxytrityl base-protected nucleoside-2-cyanoethyl-N,N-diisopropylphosphoramidites and protected nucleosides linked to controlled-pore glass supports on a 0.2 micro mol scale, according to protocols supplied by Applied Biosystems Inc.

Alternatively, the oligonucleotide sequences may be prepared by manual methods as described by Atkinson and Smith in 'Oligonucleotide Synthesis, a Practical Approach' (M. T. Gait, Editor, IRL Press, Oxford, Washington DC, pages 35–81).

In detail, the preparation of the oligonucleotide sequences by use of the Applied Biosystems 380A DNA synthesiser was effected as follows:

Each oligonucleotide, after cleavage from the solid support and removal of all protecting groups, was dissolved in water (1 ml). A solution of 3M sodium acetate (pH5.6; 40 µl) and ethanol (1 ml) was added to the oligonucleotide solutions (400 µl) and the mixtures stored at −70° C. for 20 hours. The resulting precipitates were collected by centrifugation (13,000 rpm for 10 minutes) and the pellets washed with ethanol:water (7:3) (200 µl) then dried briefly in vacuo and dissolved in water (15 µl) and 10 µl of a formamide/dye mix. (10 mM NaOH, 0.5 mM EDTA, 0.01% Bromophenol Blue, 0.01% xylene cyanol, 80% formamide.

The oligonucleotides were purified on a 10% polyacrylamide gel in 50 mM Tris-borate (pH8.3) containing 8.3M urea. Oligonucleotides of correct length were identified by UV shadowing (Narang et al, 1979 in Methods in Enzymology Vol 68, 90–98)—normally the most prominent band—excised from the gel and electroeluted in 5 mM tris-borate (pH 8.3) at 300 mV for 3–4 hours. The aqueous solutions were concentrated to about 200 µl by treatment with n-butanol (mix, spin and removal of the upper organic layer). The purified oligonucleotides were precipitated at −70° C. for 20 hours from a 0.3M sodium acetate solution by addition of ethanol (2.5 volumes).

Assembly of gene

Oligonucleotides SEQ ID No2 - SEQ ID No 17 (400 pM of each) [as defined hereinafter] were phosphorylated with T4 polynucleotide kinase (3.6 units) for 2 hours at 37° C. in 25 µl of a solution containing ATP (800 pM containing 25 pM gamma- $^{32}$p ATP), 100 µM spermidine, 20 mM MgCl$_2$, 50 mM Tris-HCl (pH9.0) and 0.1 mM EDTA. The solutions were heated at 100° C. for 5 minutes to terminate the reactions, then mixed in pairs as shown in Table 1 to give duplexes A to I (Oligonucleotides SEQ ID No 1 and SEQ ID No 18 (400 mM in 25 µl) were used unphosphorylated). 0.3M Sodium acetate (pH5.6, 200 µl) and ethanol (850 µl) were added and the duplexes precipitated at −20° C. for 20 hours. The resulting precipitates were collected by centrifugation and washed with ethanol:water (7:3) then dissolved in water (50 µl). The pairs of oligonucleotides were annealed together by first heating the solutions to 100° C. for 2 minutes in a boiling water bath. The bath was then allowed to cool slowly to 40° C. (about 4 hours). Solutions containing 3 pairs of duplexes were combined as shown (see Table 1), to give groups I to III lyophilised and dissolved in 30 µl of a solution containing T4 DNA ligase (1 unit; BRL), 50mM Tris (pH7.6), 10 mM magnesium chloride, 5% (w/v) PEG 8000, 1 mm ATP, 1 mm DTT. (BRL, Focus Vol 8 no 1 Winter 1986) and the DNA ligated at 30° C. for 5 minutes followed by 20 hours at 16° C. 3M Sodium acetate (20 µl) and water (150 µl) was added and the product precipitated by addition of ethanol (750 µl) and cooling to −20° C. for 20 hours. The precipitate was collected by centrifugation and washed with ethanol (1 ml) then dissolved in water (15 µl) and formamide/dye mix (10 µl) and purified on a 10% polyacrylamide gel in 50 mM Tris-borate (pH8.3), 1 mM EDTA and 8.3 M urea. Bands for strands of appropriate lengths (173-186 bases) were identified by autoradiography and isolated together by electroelution from a single gel slice as described above for individual oligonucleotide sequences. The DNA strands were annealed by first heating an aqueous solution (50 µl) at 100° C. for 2 minutes, then allowing it to cool to 40° C. over 4 hours. Groups I, II and III were ligated together essentially as described for the group preparation to give as the product, the gene sequence shown in FIG. 2. After precipitation, the gene was phosphorylated with T4 polynucleotide kinase as described previously for individual oligonucleotides, then dissolved in water (20 µl).

The synthetic gene described above, was cloned into the plasmid vector, pSTP1 (Windass et al, Nucleic Acids Research (1983) Vol 10, p6639.

For vector preparation, 10 µg of STP1 was dissolved in water (37.5 µl) and 10×B restriction buffer (4.5 µl) (BCL). the restriction endonuclease SalI (3 µl) (BCL, 8 units/µl) was added and the mixture incubated at 37° C. for 1 hour until linearised plasmid was predominant over supercoiled and nicked circular forms. The DNA was precipitated with ethanol at 4° C. for 30 minutes, washed with ethanol:water (7:3) then dissolved in water (39.5 µl), 10×H buffer (4.5 µl) (BCL). The restriction endonuclease EcoRI (1 µl) (BCL, 90 units/µl) was added and the mixture incubated at 37° C. for 1 hour until the large EcoRI-SalI fragment was predominant. The DNA was precipitated at −20° C. for 20 hours, washed with ethanol:water (7:3) then dissolved in water (20 µl)

The large EcoRI - SalI fragment was purified on a 1% preparative agarose gel and electroeluted and precipitated as described previously, then dissolved in water (20 µl). For ligation of the synthetic gene, a mixture of vector DNA (2 µl of the EcoRI - SalI fragment solution), synthetic gene (5 µl of the aqueous solution described previously, 5× ligase buffer (6 µl-250 mM Tris pH7.6 50 mM MgCl$_2$, 25% W/V PEG8000, 5 MM ATP, 5 mM DTT exBRL) water (15 µl) and T4 DNA ligase (2 µl, 1U/µl) was incubated at 16° C. for 4 hours. The DNA mix was used directly (either 1 µl of neat ligation mix or 2 µl of ligation mix diluted 5× with water) to transform E. coli strain HB101. The DNA mixture (1 or 2 µl) was added to competent E. coli HB101 cells (20 µl, BRL) on ice and the mixture incubated on ice for 45 min then heat shocked at 42° C. for 45 seconds. After 2 min on ice, 100 µl of SOC buffer (Bactotryptone 2%; Yeast Extract 0.5%; NaCl 10 mM; KCl 12.5 mm; MgCl$_2$, MgSO$_4$ 20 mm (10 mm each); glucose 20 mm) was added and the mixture incubated at 37° C. for 1 hour. aliquots of suspensions were plated onto L plates with 50 µl/ml ampicillin. transformants were screened for the presence of cloned synthetic gene by colony hybridisation analysis using standard methods described in "Molecular Cloning: A Laboratory Manual" by Maniatis et al (Cold Spring Harbor) and in UK Patent Application No 8502605. A total of 100 colonies were streaked onto filters (Schleicher and Schuell), grown at 37° C. for 20 hours, lysed and baked. The filter was hybridised at 65° C. for 20 hours with a radioactive probe prepared from oligonucleotide sequence SEQ ID No 1 by use of a random-label kit (Pharmacia). Five colonies 1-5 giving a positive hybridisation signal were grown up in L broth at 37° C. for 20 hours on a small scale (100 ml) and plasmid DNA b) Cloning of the synthetic gene for human G-CSF

TABLE 1

| DUPLEX | OLIGONUCLEOTIDE | NUMBER OF BASES IN | |
|---|---|---|---|
| | | TOP STRAND | BOTTOM STRAND |
| A | SEQ ID No 1 + SEQ ID No 2 | 62 | 64 |
| B | SEQ ID No 3 + SEQ ID No 4 | 60 | 60 |
| c | SEQ ID No 5 + SEQ ID No 6 | 48 | 51 |
| D | SEQ ID No 7 + SEQ ID No 8 | 63 | 60 |
| E | SEQ ID No 9 + SEQ ID No 10 | 63 | 63 |
| F | SEQ ID No 11 + SEQ ID No 12 | 60 | 63 |
| G | SEQ ID No 13 + SEQ ID No 14 | 63 | 60 |
| H | SEQ ID No 15 + SEQ ID No 16 | 60 | 60 |
| I | SEQ ID No 17 + SEQ ID No 18 | 55 | 53 |
| I | A + B + C | 170 | 175 |
| II | D + E + F | 186 | 186 |
| III | G + H + I | 178 | 173 | prepared by centrifugation in a caesium chloride gradient essentially as described in "Molecular Cloning; A Laboratory Manual" by Maniatas et al (Cold Spring Harbor).

The DNA was sequenced by the standard dideoxy chain-termination method as described by Sanger et al in Proc. Nat. Acad Sci. USA 74, 5463–5467 (1977) using a Sequenase (Trade Mark) kit (United States Biochemical Corporation). Oligonucleotides SEQ 1D No 19 to SEQ 1D No 23 (as defined hereinafter and see Table 2) were used as sequencing primers.

TABLE 2

| CODE | PRIMING SITE |
|---|---|
| SEQ ID No 19 | 214–234 top strand |
| SEQ ID No 20 | 333–353 top strand |
| SEQ ID No 21 | 375–395 bottom strand |
| SEQ ID No 22 | 207–227 bottom strand |
| SEQ ID No 23 | 69–93 bottom strand |

The plasmid DNA from clone 5 contained the DNA sequence shown in FIG. 2. The plasmid (pAG88) was used to transform competent cells of the following E.-coli strains by standard procedures:

HB101

CGSC 6300 (hereinafter also referred to as MSD 522)

The E. coli strains HB101 and MSD522 (CGSC 6300) are freely available. Thus for example they may be obtained from the E. coli Genetic Stock Centre, Yale University, USA. Moreover E. coli HB101 may additionally be obtained from for example BRL supplied by GIBCO Limited Unit 4, Cowley Mill Trading Estate, Longbridge Way, Uxbridge, UB8 2YG, Middlesex, England or GIBCO Laboratories, Life Technologies Inc., 3175 Staley Road, Grand Island, N.Y. 14072, USA. The genotype of strain HB101 is described in the aforementioned "Molecular Cloning—A Laboratory Manual" as Sup E44 hsd S20 ($r_B^- m_B^-$)rec A 13 ara-14 F$^-$leu 6 thi-1 proA2 lac Y1 gal K2 rps L20 xyl$^-$5 mtl$^-$1. The genotype of MSD 522 (CGSC 6300) is set out in Example 13.

c) Cloning of the gene for human G-CSF into an expression vector

The gene described above was cloned in the plasmid pICI 0020 as described in Example 1(c) to yield the expression plasmid pICI 1056.

d) Fermentation

The plasmid pICI 1056 was transformed and fermentation effected as described in Example 1(e) to achieve expression of human G-CSF.

e) Purification

Purification was effected as described in the second purification procedure developed to yield larger quantities of hu G-CSF set out on pages 48 and 49 of PCT Patent Publication No. WO 87/01132 with final dialysis being effected against phosphate buffered saline.

REFERENCE EXAMPLE 2

Preparation of genes for derivatives of human G-CSF by site-directed mutagenesis The phosphorothioate method of Eckstein and co-workers was used:

Taylor, J. W. et al Nucleic Acids Research (1985) Vol pp 8749–8764

Taylor, J. W. et al Nucleic Acids Research (1985) Vol pp 8765–8785

Nakamaye, K. et al Nucleic Acids Research (1986) Vol pp 9679–9698

Sayers, J. R. et al Nucleic Acids Research (1988) Vol pp 791–802

The procedure can be carried out using a kit supplied by Amersham International. The method is outlined below and incorporates changes to the original method with regard to the use of more than one mutagenic oligonucleotide and the incubation temperature for oligonucleotides of greater than 30 bases in length.

1. Annealing mutant oligonucleotide to single stranded DNA template:

| | |
|---|---|
| Single stranded DNA template (1 μ/μl) | 5 μl |
| Phosporylated mutagenic oligonculeotide (1.6 pmol/1 μl) | 2.5 μl |
| Buffer 1 | 3.5 μl |
| Water | 6 μl |

(Where two mutagenic oligonucleotides were used simultaneously, 2.5 μl (1.6 pmole/1 μl) of each phosporylated oligonucleotide was added to 5 μl single stranded DNA template (1 μg/μl) in 3.5 μl Buffer 1 and 3.5 μl water. Where 3 mutagenic oligonucleotides were used 2.5 μl (1.6 pmol/μl) of each phosporylated oligonucleotide was added to 5 μl single stranded DNA (1 μg/μl in 3.5 μl Buffer 1 and 1 μl water). The above ingredients were placed in a capped tube in a 70° C. water bath for 3 minutes if the oligonucleotide was <30 bases in length or in a boiling water bath for 3 minutes if the oligonucleotide was >30 bases in length. The tube was then placed in a 37° C. water bath for 30 minutes.

2. Synthesis and ligation of mutant DNA strand:

| To the annealing reaction were added | |
|---|---|
| MgCl$_2$ solution | 5 μl |
| Nucleotide mix 1 (contains dCTP alpha S) | 19 μl |
| water | 6 μl |
| Klenow fragment (6 units) | 1.5 μl |
| T4 DNA ligase (5 units) | 2 μl |

The above ingredients were placed in a 16° C. water-bath and left overnight.

3. Removal of single stranded (non-mutant) DNA using disposable centrifugal filter units.

To the reaction from Step 2 the following ingredients were added:

| | |
|---|---|
| Water | 170 μl |
| 5M NaCl | 30 μl |

The 250 μl sample was added to the top half of the filter unit and centrifuged at 1500 rpm for 10 minutes at room temperature in a SORVALL RT6000B bench top centrifuge using a SORVALL H1000B swing out rotor. Sample passes through two nitrocellulose membranes which bind the single stranded DNA leaving the double stranded DNA to pass through to the collection tube below.

100 μl of 500 mM NaCl were added and respun for 10 minutes to wash through any remaining RF DNA.

The following ingredients were added to the filtrate:

| | |
|---|---|
| 3M Sodium Acetate (pH 6.0) | 28 μl |
| Cold Ethanol (−20° C.) | 700 ul |

The mixture was placed in a dry ice and ethanol bath for 20 minutes and centrifuged in an Eppendorf microfuge for 15 minutes. The pellet was then resuspended in 10 μl buffer 2.

4. Nicking of the non-mutant strand using Nci I. To the reaction mix from step 3, was added 65 μl Buffer 3 and 8 units Nci I (1 μl). The mixture was placed in a 37° C. water bath for 90 minutes.

5. Digestion of non-mutant strand using exonuclease III

| To the reaction mix from step 4 was added | |
|---|---|
| 500 mM NaCl | 12 μl |
| Buffer 4 | 10 μl |
| Exonuclease III (50 units) | 2 μl |

The mixture was placed in a 37° C. water bath and incubated for 30 minutes at 37° C., 50 units of exonuclease III will digest approximately 3,000 bases in 30 minutes). The mixture was then placed in a 70° C. water bath for 15 minutes to inactivate the enzymes.

6. Repolymerisation and ligation of the gapped DNA.

| To the reaction mix from step 5 was added | |
|---|---|
| nucleotide mix 2 | 13 μl |
| MgCl$_2$ solution | 5 μl |
| DNA polymerase I (4 units) | 1 μl |
| T4 DNA ligase (2.5 units) | 1 μl |

The mixture was placed in a 16° C. bath for 3 hours.

7. Transformation of competent host *E. coli* TG1 cells with the DNA:

300 μl of freshly prepared competent *E. coli* TG1 cells (prepared of freshly prepared competent *E. coli* TG1 cells (prepared following the method of Mandel and Higa) were transformed with 20 μl of the reaction mix from step 6 (in duplicate). The transformants were plated out in a lawn of log phase TG1 cells in TY Top agar on TY plates and incubated overnight at 37° C.

The *E. coli* strain TG1 is freely available from for example the *E. coli* Genetic Stock Centre, Yale University, USA and from Amersham International plc, Amersham Place, Little Chalfont, Amersham, Buckinghamshire HP7 9NA, England as supplied in their "in vitro" mutagenesis system, oligonucleotide directed kit (Product code RPN 1523).

REFERENCE EXAMPLE 3

G-CSF Bioassay

A factor dependent cell line, Paterson—G-CSF (FDCP-G), obtained from the Paterson Institute, Manchester, England was cloned by limiting dilution in the presence of G-CSF. A G-CSF responsive clone, designated clone E7, was used to determine human recombinant G-CSF activity. $2.5 \times 10^3$ FDCP-G clone E7 cells in 100 μl of RPMI 1640+10% FCS was added to an equal volume of RPMI 1640+10% FCS containing G-CSF. Each G-CSF sample was measured over 10 doubling dilutions. The final volume of RPMI 1640 (see Moore GE et al (1967) JAMA, 199, 519)+10% FCS (foetal calf serum) in each well of 96-well microtitre plate was 200 μl. The microtitre plate was incubated at 37° C. in 5% $CO_2$ in a humidified incubator for 4 days. 1.0 μCi of titrated thymidine was added per well and incubated over the final 6 hours. Cells were harvested onto glass fibre filter papers and the level of radioactivity determined by liquid scintillation counting. The level of tritiated thymidine incorporation was found to be directly proportional to the amount of G-CSF present. The FDCP-G clone E7 assay was calibrated using recombinant human G-CSF obtained from Amersham International with a declared specific activity of 108 units/mg of protein.

The potencies of G-CSF samples were determined by comparision to a standard of known activity.

The units of G-CSF activity per ml were calculated according to the following formula:

| Dilution of G-CSF standard giving 50% maximal increase in $^3$H-thymidine incorporation | Dilution of sample giving 50% maximal increase in $^3$H-thymidine incorporation | × | Units/ml activity in G-CSF standard |
|---|---|---|---|

REFERENCE EXAMPLE 4

Solution Stability of G-CSF and derivatives thereof

Appropriate dilutions of the stock solution of G-CSF and derivatives in phosphate buffered saline (PBS) at 4° C. described in Example 11 were tested for solution stability. Solutions of 1 mg/ml, 5 mg/ml and sometimes 10 mg/ml of protein in PBS were incubated at 37° C. for 14 days. Solutions were inspected visually at regular intervals for signs of precipitation. After 14 days each solution was centrifuged at 14,000rpm for 20 minutes, the supernatant removed by decantation and the pellet re-dissolved in PBS containing 1% w/v N-lauroyl sarcosine. The total protein content in each supernatant and re-dissolved precipitate was estimated by $A_{280}$ measurements and the monomer content in each was estimated by reverse phase HPLC. These were expressed as a percentage of the corresponding data given by solutions at the start of incubation and by a 1 mg/ml solution incubated at 4° C. for 14 days. Variations between total protein and monomer estimates were observed only in some of the re-dissolved pellets. The percentage protein remaining in solution in the supernatants from each starting concentration is summarised in the Table.

The specific activity of the product in each supernatant after incubation was shown to be the same as in the starting solution, and no differences were observed on PAGE-SDS under reducing or non-reducing conditions.

The following results were obtained:

| G-CSF Derivatives | Spec. Act. (U/mg × 10$^9$) | Solution Stability* | | |
|---|---|---|---|---|
| | | 1 mg/ml | 5 mg/ml | 10 mg/ml |
| [Met$^{-1}$]hu G-CSF | 0.4 | 23 | nd | nd |
| [Met$^{-1}$, Ser$^{17}$]hu G-CSF | 1.0 | 80 | 20 | nd |
| [Met$^{-1}$, Ser$^{17,27}$]hu G-CSF | 1.5 | 80 | 40 | nd |
| [Met$^{-1}$, Arg$^{11}$, Ser$^{17,27,60,65}$] hu G-CSF | 1.2 | 98 | 94 | 92 |
| [Met$^{-1}$, Ser$^{17,27}$, Glu$^{111}$, | 2.7 | 100 | 72 | 50 |

-continued

| G-CSF Derivatives | Spec. Act. (U/mg × 10$^9$) | Solution Stability* 1 mg/ml | 5 mg/ml | 10 mg/ml |
|---|---|---|---|---|
| Ser$^{115,116}$]hu G-CSF | | | | |
| [Met$^{-1}$, Ser$^{17,27}$, Arg$^{11,165}$, Lys$^{58}$] hu G-CSF | 1.2 | 92 | 77 | 47 |
| [Met$^{-1}$, Glu$^{15}$, Ser$^{17,27}$, Ala$^{26,28}$, Lys$^{30}$]hu G-CSF | 1.0 | 100 | 100 | 94 |
| [Met$^{-1}$, Ser$^{17,27}$, Lys$^{49,58}$, Ala$^{44,51,55}$] hu G-CSF | 1.0 | 84 | 69 | 44 |
| [Met$^{-1}$, Arg$^{11}$, Glu$^{15}$, Ser$^{17,27,60,65}$, Ala$^{26,28}$, Lys$^{30}$]hu G-CSF | 2.6 | 100 | 103 | 93 |
| [Met$^{-1}$, Glu$^{15}$, Ser$^{17,27}$, Ala$^{26,28}$, Arg$^{30}$]hu G-CSF | 0.85 | 100 | 100 | 100 |
| [Met$^{-1}$, Arg$^{11,23}$, Ser$^{17,27,60,65}$]hu G-CSF | 2.5 | 100 | 98 | 88 |
| [Met$^{-1}$, Arg$^{11,34}$Ser$^{17,27,60,65}$] hu G-CSF | 1.4 | 105 | 92 | 80 |
| [Met$^{-1}$, Arg$^{11,40}$, Ser$^{17,27,60,65}$] hu G-CSF | 1.3 | 108 | 100 | 87 |
| [Met$^{-1}$, Ala$^1$, Tghr$^3$, Tyr$^4$, Arg$^{5,11}$, Ser$^{17,27,60,65}$]hu G-CSF | 1.5 | 106 | 100 | 89 |
| [Met$^{-1}$, Arg$^{11}$, Glu$^{15,111}$, Ser$^{17,27,60,65,115,116}$, Ala$^{26,28}$, Lys$^{30}$]hu G-CSF | 0.5 | 100 | 100 | 100 |
| [Met$^{-1}$, Arg$^{11,165}$, Glu$^{15}$, Ser$^{17,27,60,65}$ Ala$^{26,28}$Lys$^{30,58}$]hu G-CSF | 0.65 | 100 | 100 | 100 |
| [Met$^{-1}$, Arg$^{11}$, Glu$^{15}$, Ser$^{17,27,60,65}$, Ala$^{26,28,44,51,55}$, Lys$^{30,49,58}$] hu G-CSF | 0.20 | 100 | 100 | 95 |
| [Met$^{-1}$, Arg$^{11,165}$, Glu$^{15,111}$, Ser$^{17,27,60,65,115,116}$, Ala$^{26,28,44,51,55}$, Lys$^{30,49,58}$] hu G-CSF | 0.05 | 100 | 100 | 100 |
| [Met$^{-1}$, Arg$^{11}$, Ser$^{17,27}$]hu G-CSF | 0.73 | 97 | 35 | 12 |
| [Met$^{-1}$, Ser$^{17,27,60,65}$]hu G-CSF | 0.71 | 100 | 94 | 86 |
| [Met$^{-1}$, Arg$^{11}$, Ser$^{17,27,60}$]hu G-CSF | 0.81 | 94 | 65 | 32 |
| [Met$^{-1}$, Arg$^{11}$, Ser$^{17,27,65}$]hu G-CSF | 0.80 | 100 | 96 | 89 |
| [Met$^{-1}$, Ser$^{17,27,60}$]hu G-CSF | 0.80 | 95 | 68 | 36 |
| [Met$^{-1}$, Ser$^{17,27,65}$]hu G-CSF | 0.83 | 100 | 94 | 90 |

*percentage left in solution in PBS after 14 days at 37° C. (established by UV; by HPLC available)

nd means not done

[Met$^{-1}$,Ser$^{17}$]hu G-CSF may be obtained as described in Reference Example 5.

The above results demonstrate that modifications of the present invention improve solution stability without loss of G-CSF activity, [Met$^{-1}$,Ser$^{17}$]hu G-CSF in a concentration of 5 mg/ml starting to precipitate out within 3 hours.

REFERENCE EXAMPLE 5

Preparation of [Ser$^{17}$]hu G-CSF

The procedure described in Example 2 for the preparation of [Met$^{-1}$,Ser$^{17,27}$]hu G-CSF was repeated except as follows:

1) The duplex for phosphorylation was prepared from oligonucleotide sequences SEQ ID Nos 24, 25, 3 and 4, the sequences SEQ ID Nos 3 and 4 respectively replacing sequences SEQ ID Nos 26 and 27 employed in Examples 1 and 2.

2) The duplex referred to in (1) was phosphorylated with T4 polynucleotide kinase, but was digested with SnaBI (10 units) in 1×M buffer (BCL; 30 μl) for 2 hours at 37° C.

3) Following purification with ethanol, the 72 bp EcoRI-SnaBI fragment was purified as opposed to the 143 bp EcoRI-MstII fragment.

4) The synthetic EcoRI-SnaBI fragment was cloned into the plasmid vector pAG88 as described in Reference Example 1 and for vector preparation pAG88 was digested with SnaBI (20 units; BCL) in 1×M buffer (BCL; 100 μl) for 2 hours at 37° C. instead of Mst II in 1×H buffer.

5) Following precipitation with ethanol, the large EcoRI-SnaBI fragment was purified on a 1% agarose gel as opposed to the large EcoRI-MstII fragment.

6) The plasmid containing the gene for [Ser$^{17}$] hu G-CSF was designated pICI 1105.

REFERENCE EXAMPLE 6

Construction of pICI 0080 a) Construction of pTB357 (also referred to herein as pLB 004

Plasmid pTB357 utilises a repressed tetracycline resistance determinant, as found on the naturally-occurring plasmid RP4. This repressed system shuts off expression of the tetA gene in the absence of tetracycline whereas most drug resistant mechanisms have constitutive expression.

The tet locus was first mapped on RP4 by Barth and Grinter (*J.Mol. Biol.* 113: 455–474, 1977). This was shown to consist of adjacent genes: tetA, the structural resistance gene and tetR, the repressor gene and this region has been sequenced (Klock et al, *J. Bacteriol:* 161:326–332, 1985). These genes are located on adjacent BglII-SmaI and SmaI-SmaI fragments. The BglII site is unique in RP4 but there are five SmaI sites (Lanka, Lurz and Furste, Plasmid 10: 303–307, 1983).

i) Cloning the tetA+tetR genes

The plasmid RP4 is well documented (Datta et al, *J. Bacteriol* 108: 1244, 1971) and is freely available. Furthermore the plasmid RP4 has been deposited with the National Collection of Type Cultures, 61 Colindale Avenue, London, NW9 5HT under accession nos. 50078 and 50437. E. coli strains containing this plasmid were grown in selective broth cultures and plasmid DNA was isolated a scale-up of the Holmes and Quigley method (Holmes and Quigley, Anal. Biochem 114: 193–197, 1981). It was deproteinized by treatment with 2.5M ammonium acetate and reprecipitated with isopropanol. This plasmid DNA was treated, according to the supplier's recommended conditions, with restriction enzyme BglII and cut to completion. It was then partially cut by XmaI by using diluted enzyme and short incubation times. XmaI is an isoschizomer of SmaI but which produces 4-nucleotide cohesive ends at its cut sites.

The vector plasmid pUC8 (Yanisch-Perron, Vieira and Messing, Gene 33: 103–119, 1985) was similarly prepared and cut with BamHI and XmaI to completion. The RP4 fragments were cloned into this vector by ligation with T4 ligase at 12° C. for 16 hours. This was used to transform E. coli C600 made competent by the calcium chloride method (Maniatis et al, Cold Spring Harbor Laboratory, 1982). Cultures were then plated onto medium which selected for tetracycline resistance.

E. coli C600 is freely available from numerous sources including many culture collections such as the E.coli Genetic Stock Centre, Yale University, USA under accession No GCSC 3004. The genotype of E.coli C600 is K12 thr-1 leuB6 thi-1 hsdS1 lacY1 tonA21 λ⁻supE44.

Several colonies with this resistance were checked for the expected phenotype (ampicillin and tetracycline resistance but not the kanamycin resistance indicative of RP4 itself). Colonies with the correct resistances were subjected to clone analysis by isolating plasmid DNA (Holmes and Quigley method). These preparations were cut with EcoRI and HindIII and analysed by gel electrophoresis. This established the size of the cloned insert which was found to be the 2.45 kb predicted for the BglII - XmaI - XmaI fragment from RP4. A clone carrying this fragment containing the tetA and tetR genes was designated pTB344.

ii) Removal of the tet gene from pAT153

It was necessary to remove the tet gene from the vector plasmid pAT153 before inserting the tetA+tetR cassette from RP4 to prevent gene duplication which can be a source of genetic instability. Also the tet gene may not be effectively suppressed byt he non-cognate tetR. The removal was done by isolating plasmid pAT153 DNA and cutting it with EcoRI and AvaI. Between these sites, synthetic olignucleotides with the sequence SEQ ID No.59 and SEQ ID No: 66:

5' AATTCGCATGCGGATCCATCGATC3'
3'GCGTACGCCTAGGTAGCTAGAGCC5' were clonded. These fit the EcoRI and AvaI cohesive ends and contain SphI, BamHI and ClaI sites in addition. After transformation and selected, colonies were tested for the loss of the teracycline resistance determinant. Plasmid DNA from one clone was sequenced to confirm that the predicted sequence was correct. This plasmid was designated pCH19.

iii) Insertion of the tetA+tetR genes

The tetA and tetR genes were isolated from pTB344 on an EcoRI to PstI fragment. The pUC8 vector was destroyed by curring with SspI because it carries the same selection determinant (ampicillin resistance) as pCH19. Plasmid pCH19 DNA was cut with EcoRI and PstI and then ligated with the 2.45 kb fragment carrying the tet genes. This was used to transform E.coli C600, the culture being plated out under selection for tetracycline reistant colonies. The insertion of the tet genes was designed to replace most of the bla genes in pCH19 which should thus lose its ampicillin resistance determinant. Loss of ampicillin resistance from the transformants was confirmed. A few clones were then used to isolate plasmid DNA which was subjected to restriction analysis. This confirmed that the constructed plasmid had the intended structure. It was designated pTB351.

iv) Insertion of the cer sequence

The naturally-occuring plasmid ColEI is very stably maintained in E.coli, whereas its derivatives pBR322 and pAT153 are not. Summers and Sherratt (Cell, 36: 1097–1103, 1984) demonstrated that this was due to the derivatives not containing a short (283 bp) sequence called cer which is present in the parent plasmid. This sequence contains a site-specific plasmid multimer-resolution system which prevents the accumulation of plasmid multimers formed by homologous recombination. Such multimers have a deleterious effect on the process of partition which normally ensures stable inheritance of daughter plasmids during bacterial cell division.

The cer sequence (Summers, Det al MGG, 201, p334–338, 1985) was isolated from plasmid pKS492 (provided by D. Sherratt) as a 289 bp fragment by cutting with BamHI and TaqI. The plasmid pTB351 was isolated as DNA from a dam strain of E. coli to prevent its ClaI site being blocked by the dam+ methylation system. This DNA was cut with BamHI and ClaI (both these sites having been introduced on the synthetic oligonucleotide for this cloning). The cer fragment was ligated with the cut vector and then used to transform E. coli C600, selection being made for tetracycline reisistance. Transformant colonies were subjected to clone analysis by AvaI restriction and gel electrophoresis. The presence of an extra DNA band of about 300 bp indicated the acquisition of the cer fragment. Further restriction analyses were used to confirm that resultant plasmids had the correct structure. One of these was designated pTB357 (FIG. 5) and also designated pLB004.

b) Plasmid pCH101

Figures 6, 7:
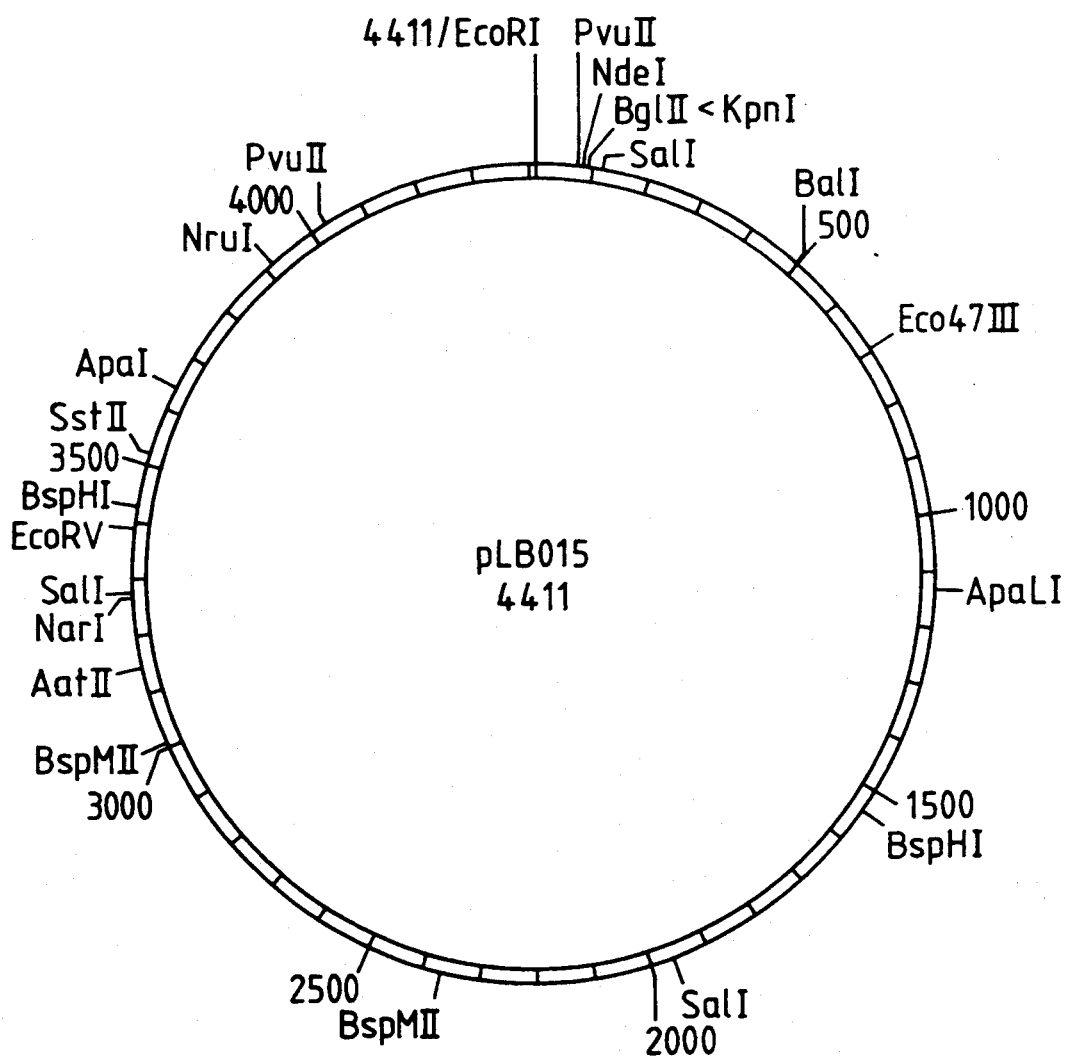
FIG. 6 shows the nucleotide sequence of the EcoRI-SalI fragment referred to in Reference Example 6(b) but omitting the interferon α$_2$ gene sequence.
FIG. 7 shows a restriction map of pLB015 (also referred to herein as pICI 0080)

The plasmid pCH101 corresponds to pICI 0020 (see Example 1c) except that the EcoRI-SalI fragment (see FIG. 1) is replaced by a fragment consisting of the SEQ ID No 53 (see FIG. 6 also) and the interferon $\alpha_2$ gene sequence as described by Edge M.D. et al, Nucleic Acids Research 1983, Vol11, p6419–6435. In this regard the 3'-terminal ATG codon of SEQ ID No 53 immediately precedes the TGT codon which codes for cysteine (amino acid 1) in the interferon $\alpha_2$ sequence of the above-mentioned Edge M.D. et al Nucleic Acids Research reference. The 5' nucleotide sequence GATC-CATG and the complementary 3' nucleotide sequence GTAC are thus omitted from the nucleotide sequence of the aforementioned reference.

c) Insertion of an Expression Cassette into pTB357

An expression cassette consisting of the trp promoter, a ribosome binding site and the interferon $\alpha_2$ gene was isolated from plasmid pCH101 (see b above) on an EcoRI to SphI restriction fragment. This was ligated into the production vector (pTB357) (see (a) above) similarly cut with EcoRI and SphI. This DNA was used to transform a competent culture of E. coli C600 and tetracycline resistant colonies were isolated. A few of these were tested by DNA clone analysis for the acquisition of the SstI restriction site carried on the expression cassette. Clones positive in this respect were further tested by restriction mapping to check that the expected construct was correct. They were also checked for the conferred capacity to produce interferon $\alpha_2$ protein as analysed on a polyacrylamide-SDS gel stained with Coomassie blue. One such confirmed clone was designated pLB005.

d) Insertion of T4 transcription terminator into pTB 244

The T4 transcription terminator sequence in the form of the SalI to HindIII fragment (67 bases pairs long) (see SEQ ID No. 51 SEQ ID No: 61 and FIG. 4a) was inserted into the multicloning site of an intermediate vector pTB 244 (described in European Patent Publication No. 237,269) between its SalI and HindIII sites. Clone analysis was used to confirm the structure of this construct (pTB244. T4 ter). From this vector, an SstI to SphI fragment containing most of the multicloning site and the T4 terminator was then isolated. This was inserted into pLB005 similarly cut with SstI and SphI thereby substituting the interferon $\alpha_2$ gene but leaving a cassette consisting of the trp promoter, multicloning site and T4 terminator. This construct was confirmed by clone analysis and the plasmid designated pLB013.

e) Substitution of the multicloning site

The multicloning site in pLB013 is not ideal for this vector in several respects: the SalI, BamHI and SmaI sites are not unique but exist elsewhere on the plasmid. This fragment was therefore excised by cutting with SstI and XbaI (both unique) and synthetic oligonucleotides with the sequence of SEQ ID No. 54:and SEQ ID NO: 63 and with NdeI designed to provide the ATG start codon of the gene to be expressed.

REFERENCE EXAMPLE 7

Figure 8:
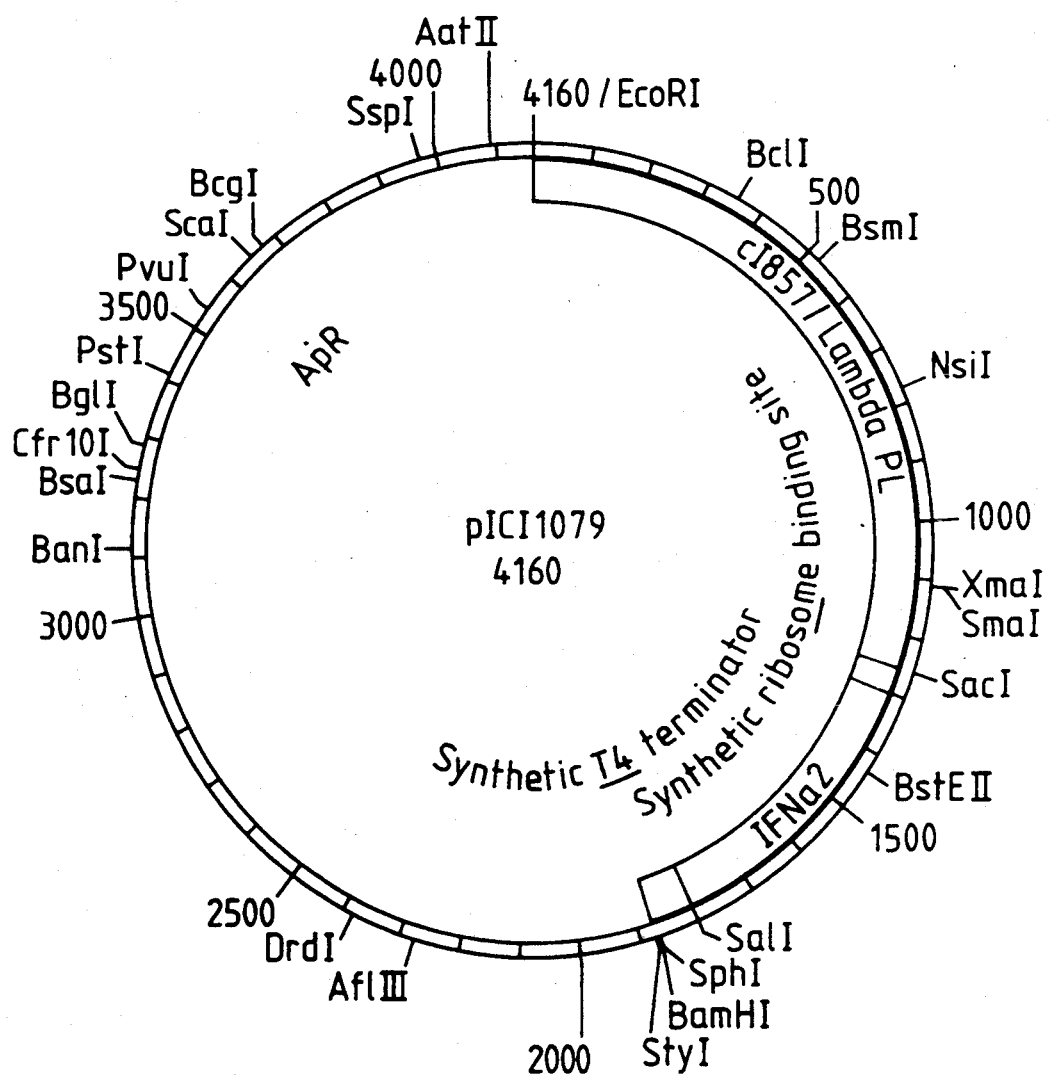
FIG. 8 shows a restriction map of pICI 1079.

Construction of plasmid pICI 1295 (also referred to as pCG300 a) Production of pCG54 from pICI1079 pICI1079 is an ampicillin resistant, pAT153-derived plasmid containing the following elements between the EcoRI and StyII restriction sites:
(i) a CI857 from phage λ;
(ii) a $\lambda P_L$ promoter;
(iii) a synthetic ribosome binding site;
(iv) a synthetic interferon $\alpha_2$ gene sequence;
(v) a synthetic transcription terminator sequence, derived from phage T4, between the SalI and StyI restriction sites. The DNA sequence of this transcription terminator is shown in FIG. 4 and SEQ ID No. 56 and SEQ ID NO: 65.

pICI1079 is illustrated in FIG. 8.

pICI1079 has been deposited under the Budapest Treaty, at the National Collections of Industrial and Marine Bacteria Limited (NCIMB), 23 St. Machar Drive, Aberdeen, AB2 1RY, Scotland, UK. (NCIMB No 40370, date of deposit 19 February 1991).

pCG54 was constructed in order to make available an expression vector containing the same promoter, ribosome binding site and transcription terminator sequences as above, ie: $\lambda p_L$, RBS7 and T4, but lacking gene sequence encoding for production of a specific protein. Such a construct would provide the facility of a basic expression vector containing essential elements allowing transcription and translation for production of any protein of interest which could be introduced into this

```
5' AGCTCCATATGGTACCAGATCTCTCGAGAGTACTT
     GGTATACCATGGTCTAGAGAGCTCTCATGAAGATC 5'
``` were inserted in its place. Clones were analysed for acquisition of the new restriction sites and then confirmed by sequencing. One such plasmid was designated pLB014. The new cloning sites inserted in this way are: NdeI, KpnI, BglII, XhoI and ScaI with the previous XbaI and SalI following them.

f) Further modification

It was discovered that the adjacent SstI and NdeI sites in pLB014 could not be cut by both these restriction enzymes either simultaneously or sequentially presumably because of their close proximity. An additional sequence was therefore inserted between them. This was done by cutting pLB014 with SstI and KpnI and then inserting the synthetic oligonucleotide of SEQ ID No. 55 and SEQ ID No: 64.

```
5' AGCTCAGCTGCAGCATATGGTAC
       GTCGACGTCGTATAC 5'
```

Clones were analysed for acquisition of an extra PvuII or PstI site and then confirmed by sequencing. One such plasmid was designated pLB015 (=pICI 0080) (see FIG. 7). This plasmid, unlike pLB014, is efficiently cut by SstI and NdeI. This is to provide a place to insert a variety of ribosome binding site sequences correctly positioned with respect to the upstream trp promoter vector by subsequent cloning events.

Construction of the vector was initiated by restriction endonuclease cleavage of plCI1079 at its respective EcoRI and SalI sites. This cleavage step released a vector fragment containing the plCI1079 backbone complete with genes for plasmid replication and antibiotic resistance functions, plus the T4 transcription terminator sequence. The fragment was isolated by agarose gel purification steps using Geneclean for final purification of the DNA fragment.

To this vector fragment a second smaller DNA fragment of approximately 1.2 Kb in size was introduced. This second fragment may be obtained, for example by DNA synthesis or by site directed or PCR mutagenesis of the small EcoRI-SalI restriction fragment obtained from pICI1079 as described above. This second fragment contained exactly equivalent promoter and ribosome binding site sequences as originally present in pICI1079 and additionally had EcoRI and SalI sites available at its 5' and 3' termini respectively, so providing compatible termini for ligation to the pICI1079 fragment. A ligation reaction in the presence of Gibco-BRL enzyme T4 DNA ligase and its respective buffer, resulted in the formation of the construct pCG54.

Clones containing this construct were originally isolated following transformation of an aliquot of the ligation reaction mixture into E.coli competent cells of strain HB101.

Figure 9:
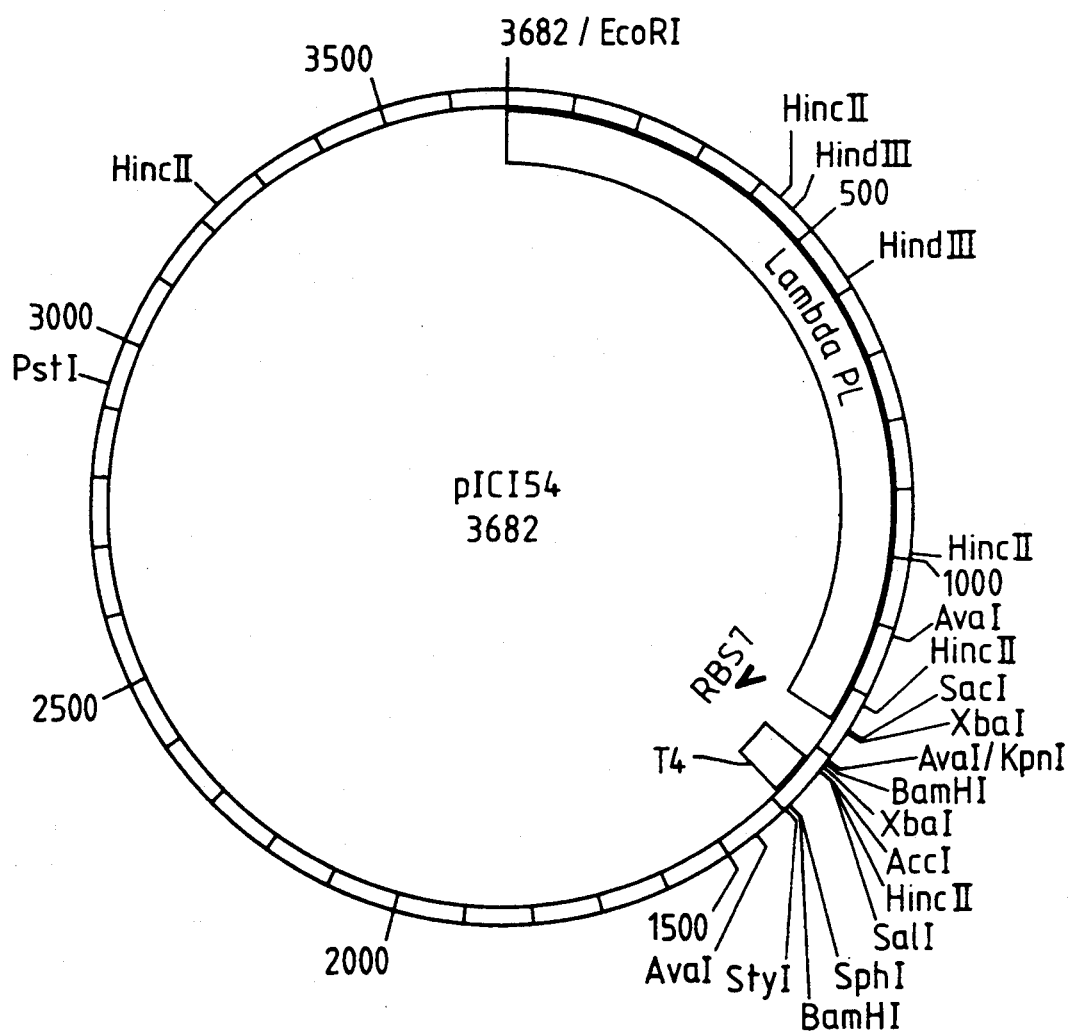
FIG. 9 shows a restriction map of pICI 54 (also referred to herein as pCG54.

The construct pCG54 recovered was 3.682 Kb in size and contained essential features as outlined on the map featured in FIG. 9.

b) Production of pCG61 from pCG54 (also referred to as pICI54)

Synthetic oligonucleotide sequences were designed so as to include both the natural sequence for the T7A3 promoter and also a sequence which would provide an effective translation initiation region to enable correct processing of any polypeptide gene sequence cloned adjacent to it. A suitable candidate sequence for this latter region was identified as RBS1, the trp ribosome binding sequence. Therefore two complimentary oligonucleotides identified as SEQ ID No.57 and SEQ ID No.58 were synthesized to generate a double stranded DNA linker incorporating the T7A3 promoter and RBS1 sequences.

Oligonucleotides were prepared as 84 mers by the standard protocol using an ABI gene synthesizer. They were designed so that in the double stranded form the synthetic fragments would have restriction endonuclease sites EcoRI and KpnI at the 5' and 3' ends respectively. Due to their length the oligomers could not be purified by means of HPLC and purification was undertaken by means of acrylamide gel electrophoresis using a 10% acrylamide: 7M Urea gel.

Prior to purification, the oligomers were first checked on a sizing gel to ensure that not only are they of the correct size but that also the samples prepared contain as their greatest proportion the oligomers required and not a high contaminating proportion of smaller secondary oligonucleotides which result as byproducts of synthesis.

The acrylamide gels were prepared by standard methods with ammonium persulphate and N,N,N',N'-tetramethylethylenediamine used as catalysts for gel polymerisation.

Sizing of the oligonucleotides required that they could be visualized after electropohoresis. It was therefore necessary to radioactively label the samples using $^{32}$p. This made it possible to assess sample quality following electrophoresis by way of autoradiography.

Oligonucleotide samples were supplied in a crude form unphosphorylated. This factor was made use of for radiolabelling purposes in that the samples could be 'hot' labelled at the 5' termini by phosphorylation using the enzyme T4 polynucleotide kinase.

Oligomers were provided from synthesis in an unphosphorylated form and so after purification each oligomer was individually subjected to a phosphorylation reaction in which ATP was used to phosphorylate the 5' end of each molecule in the presence of T4 polynucleotide kinase. (see Molecular Cloning: A Laboratory manual 2nd Edition, Sambrook, Fristch and Maniatis, p 5.68–5.71). Once phosphorylated the two complimentary oligonucleotides were annealed together to form the double strand DNA duplex containing the T7A3 promoter and the RBS1 sequence.

The vector molecule pCG54 was cleaved with restriction enzymes EcoRI and KpnI. On restriction digestion 2.3 kb vector fragment and a 1.1 kb fragment containing the $\lambda_{PL}$ promoter and RBS1 sequence are generated. This cloning step is planned to replace the $\lambda_{PL}$-$_{RBS}$1 sequence by EcoRI to KpnI synthetic fragment comprising the T7A3-RBS1 sequence. The 2.3 kb vector fragment resulting from digestion of pCG54 was purified by the usual protocol using agarose gel electrophoresis and Geneclean methodology for removal of DNA from agarose fragments.

The 84 bp EcoRI-KpnI synthetic fragment was ligated into the vector molecule prepared above and the ligated DNA used to transform E.coli HB101 cells. Selection of positive recombinant clones was by ampicillin resistance. Following transformation a number of colonies containing recombinant plasmid were selected for screening purposes.

The synthetic fragment incorporated into the vector during cloning was of a size (84 mer) such as to make restriction analysis of recombinant plasmid DNA samples inappropriate as a simple screening method. Inserts of such a small size are not readily apparent on agarose gel electrophoresis. The fragment itself contains no internal restriction endonuclease cleavage site which could be diagnostic of its presence. Initial screening of recombinant clones was therefore by the method of colony hybridisation (see Grunstein and Hogness Proc. Natl Acad. Sci 72, 3961 (1975)). Nitrocellulose filters containing immobilized plasmid DNA from the recombinant clones were hybridised against a probe prepared by random radiolabelling of the synthetic annealed oligonucleotide SEQ ID No. 57 and SEQ ID No.58. The DNA was labelled using a $\alpha^{32}$P-dCTP and incubation with Klenow polymerase at 37° C. for 2 hours. Recombinant colonies which generated a positive hybridisation reaction were selected for plasmid DNA preparation. Plasmid DNA was prepared in each case by a relatively large scale method incorporating CsCl gradient density centrifugation to ensure purity see "Molecular Cloning—A laboratory manual "second edition, Sambrook Fritsch and Maniatis (Cold Spring Harbor Laboratory, 1989) p1.42–1.52. Preparation of DNA by such a method ensures high quality material suitable for use in subsequent cloning manipulations and sequence analysis.

All plasmid DNA isolated from recombinant clones was included in a secondary screen by sequence analysis, to ensure that the oligonucleotide sequence at the cloning junctions and of the T7A3-RBS1 fragment itself was absolutely correct. The sequencing protocol used was that of Sequenase and the sequencing primer selected for use was for example pBR322 UP (pBR322 universal primer). Sequencing was effected using the Sanger dideoxy chain termination sequencing technique.

Figure 10:
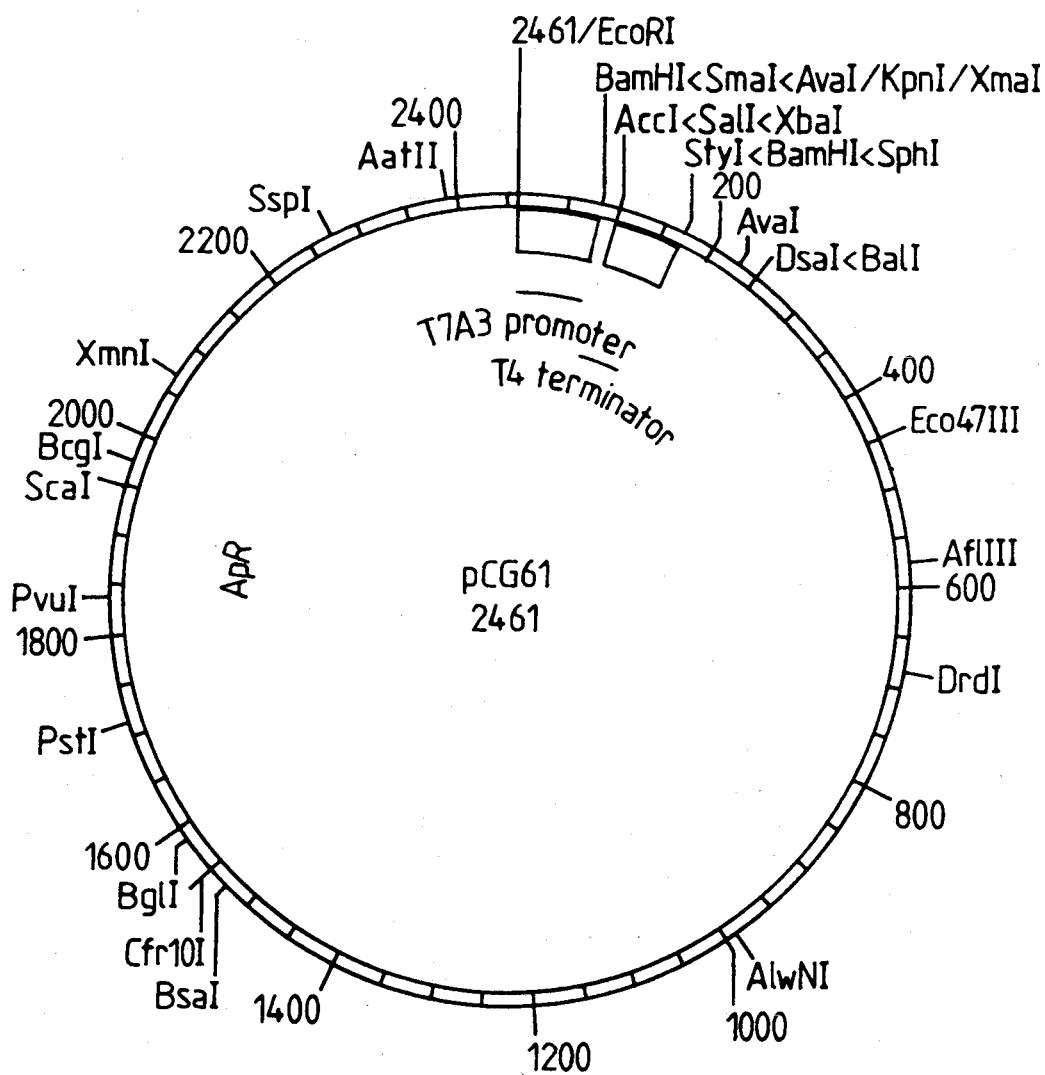
FIG. 10 shows a restriction map of pCG61.
Figure 11:
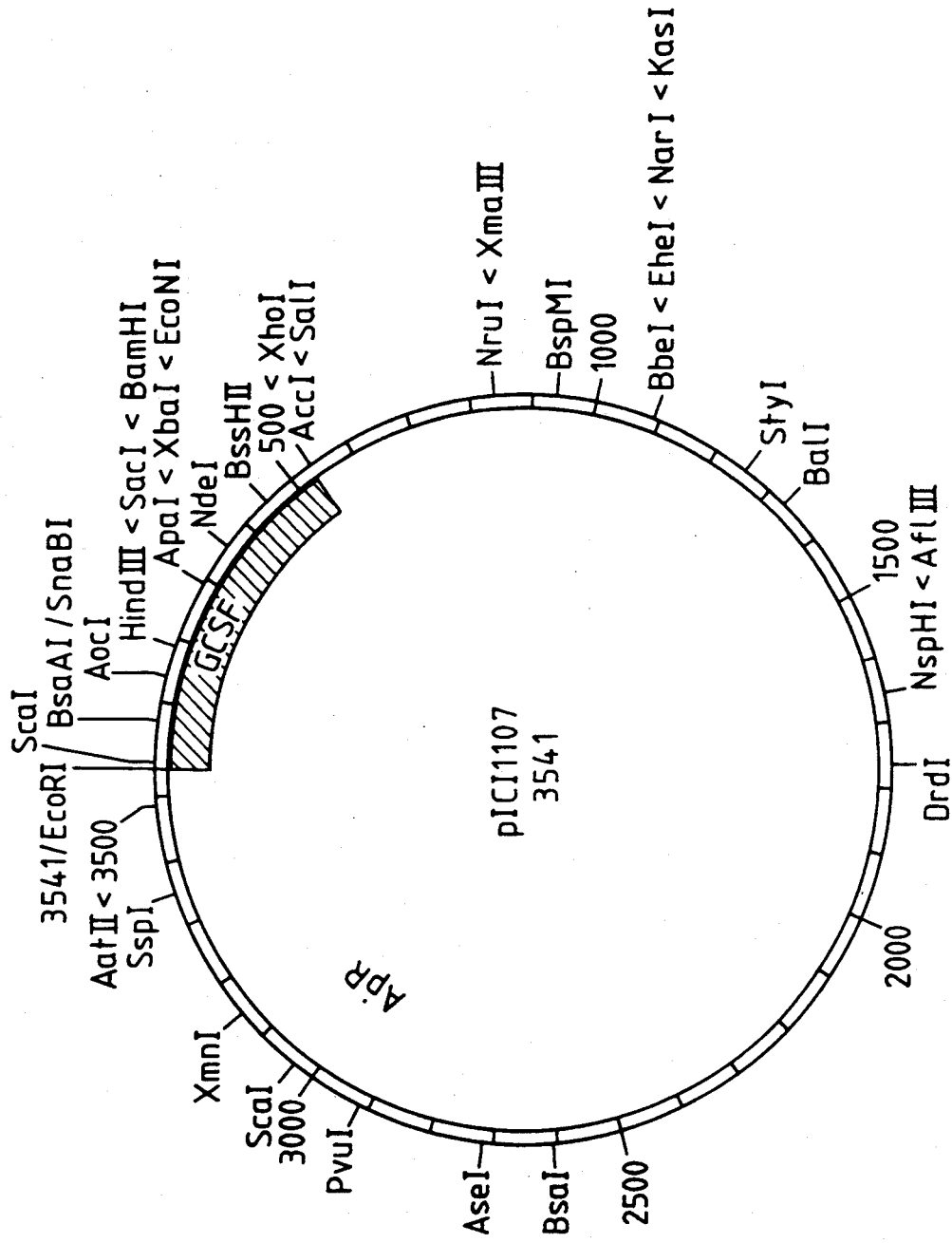
FIG. 11 shows a restriction map of pICI 1107 in which the shaded area represents the gene sequence coding for [Ser$^{17,27}$]hu G-CSF.

Clones having the correct sequence were designated as the new expression construct pCG61, and contained the T7A3 promoter, RBS1 sequence and the T4 terminator sequence (see FIG. 10).

c) Production of pCG300 (also referred to as pICI 1295) from pCG61

The sequence and synthesis steps involved in construction of the G-CSF analogue [Ser$^{17,27}$]hu G-CSF are as described in Example 1 (see FIG. 3). This G-CSF analogue sequence was isolated from a construct in which the gene had been incorporated into the plasmid pSTP1 to give pICI1107 (see Example 2). pICI1107 was digested with ScaI and the large fragment isolated following agarose gel electrophoresis and Geneclean purification. This fragment was then digested with the restriction endonuclease SalI to generate a [Ser17,27]hu G-CSF gene on a ScaI to SalI restriction fragment suitable for cloning into pCG61 (see FIG. 10).

Following restriction with SalI the required fragment was isolated using agarose gel purification techniques once again.

The vector molecule pCG61 was digested with restriction enzyme KpnI. Cleavage with this enzyme creates a 3' overhang which was then blunt-ended using the enzyme T4 polymerase see "Molecular Cloning—a Laboratory manual", Second Edition Sambrook, Fritsch and Manjarls, p5.44–5.47. T4 polymerase activity was heat inactivated by incubation at 70° C. for 30 minutes and the DNA was recovered by ethanol precipitation. The pellet was dissolved in sterile distilled water and the solubilized DNA cleaved with SalI. The KpnI (now blunt-ended) to SalI vector fragment was recovered by means of ethanol precipitation followed by agarose gel electrophoresis and purification techniques.

The ScaI to SalI [Ser$^{17,27}$]hu G-CSF fragment was then ligated into the blunt-ended KpnI to SalI vector. Ligated DNA was transformed into E.coli strain HB101. Selection of recombinant clones was for ampicillin resistance.

Initial screening of potential recombinant clones was by means of hybridisation. A radiolabelled probe was prepared by random labelling of an EcoRI to SalI fragment (containing the [Ser$^{17,27}$]hu G-CSF gene sequence) prepared from the plasmid pICI1107. This was used in hybridisation against colonies whose DNA had been immobilized onto the surface of nitrocellulose filters. Subsequently plasmid DNA was prepared from 24 clones which had been hybridised in this screen. All DNA preparations were by the rapid mini-prep method see Birnboim and Doly, Nucleic Acids Research, 7, 1513, 1979. These recombinant DNA preparations were subjected to a secondary screen by way of restriction analysis. Linearization of the DNA with BamHI, which is a unique site within the expression cassette, is indicative of the presence of the [Ser$^{17,27}$]hu G-CSF sequence.

Figure 12:
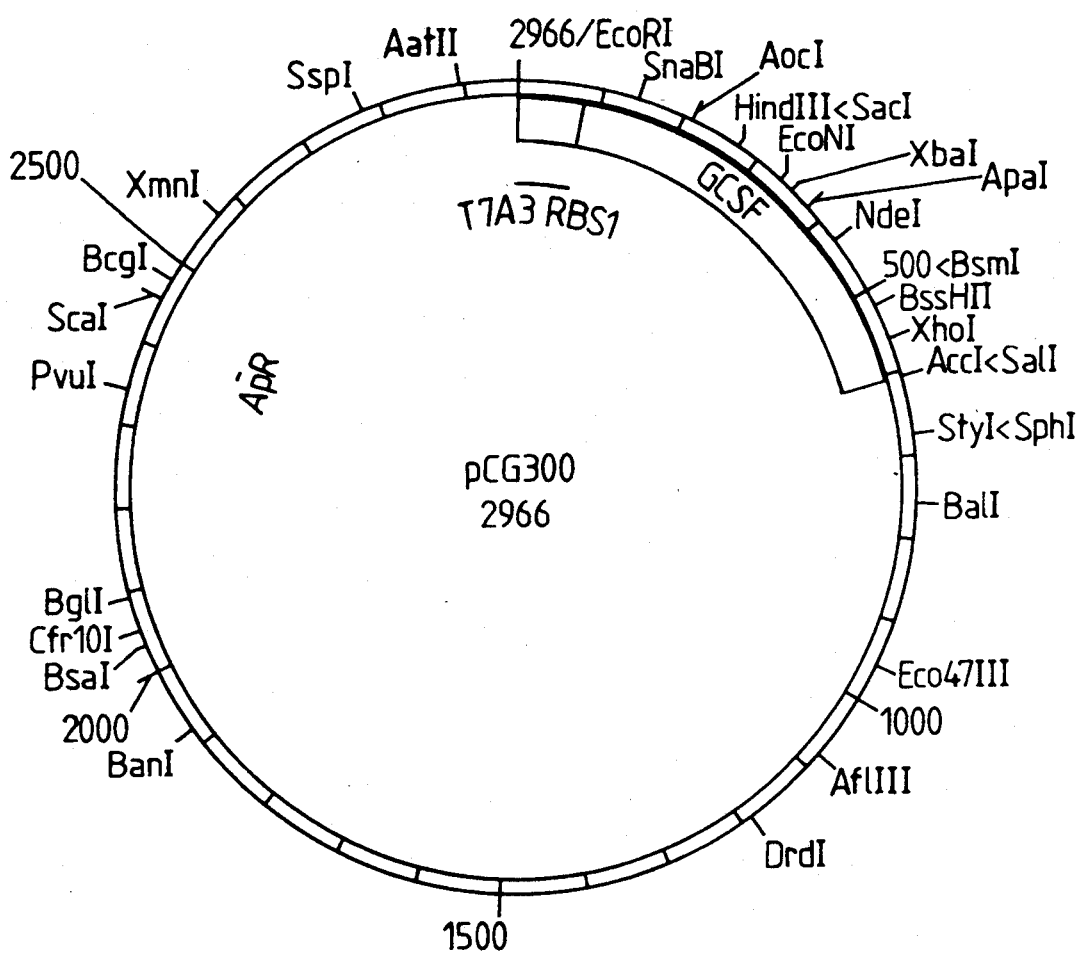
FIG. 12 shows a restriction map of pCG300 (also referred to herein as pICI 1295.

Sequence analysis was performed to confirm the presence of the [Ser$^{17,27}$]hu G-CSF gene and to verify that the base sequence at the cloning junctions and throughout the [Ser$^{17,27}$]hu G-CSF gene was correct. For this purpose large scale plasmid DNA samples were prepared from 16 recombinant clones using the CsCl gradient density centrifugation technique to ensure purity. Sequencing steps were performed in accordance with the sequence protocol and the sequencing primer selected was the pBR322 universal primer (EcoRI). Two of the recombinant clones contained the correct sequence at the ScaI end of the [Ser$^{17,27}$]hu G-CSF fragment and throughout the G-CSF peptide sequence itself. The clones were identified as expression construct pCG300 (see FIG. 12).

---

We claim:

1. A derivative of naturally occurring G-CSF having at least one of the biological properties of naturally occurring G-CSF and a solution stability of at least 35% at 5 mg/ml, the said derivative having at least $Cys^{17}$ of the native sequence replaced by a $Ser^{17}$ residue and $Asp^{27}$ of the native sequence replaced by a $Ser^{27}$ residue, and having at least one further modification selected from the group consisting of:
   a) $Pro^{66}$ of the native sequence replaced by a $Ser^{60}$ residue; and
   b) $Pro^{65}$ of the native sequence replaced by a $Ser^{65}$ residue.

2. A derivative as claimed in claim 1 selected from:
$[Arg^{11}, Ser^{17,27,60,65}]$hu G-CSF;
$[Ser^{17,27,60,65}]$hu G-CSF
$[Arg^{11}, Ser^{17,27,65}]$hu G-CSF
$[Ser^{17,27,65}]$hu G-CSF
said derivative, if desired having a presequence methionine.

3. A derivative as claimed in claim 1 wherein the further modification is selected from the group consisting of:
   a) $Gln^{11}$, $Pro^{60,65}$ of the native sequence replaced by $Arg^{11}$, $Ser^{60,65}$;
   b) $Pro^{60,65}$ of the native sequence replaced by $Ser^{60,65}$; and
   c) $Gln^{11}$, $Pro^{65}$ of the native sequence replaced by $Arg^{11}$, $Ser^{65}$.

4. A pharmaceutical composition comprising as active ingredient at least one derivative of naturally occurring G-CSF as claimed in claim 1 in association with a pharmaceutically aceeptable carrier or excipient.

* * * * *

SEQUENCE LISTING ( 1 ) GENERAL INFORMATION:

( i i i ) NUMBER OF SEQUENCES: 66

( 2 ) INFORMATION FOR SEQ ID NO:1:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
AATTCAGTAC TCCACTGGGT CCAGCAAGCT CTCTGCCGCA GTCTTTCCTG CTGAAGTGTC    60

TC                                                                   62
```

( 2 ) INFORMATION FOR SEQ ID NO:2:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
CTGTTCGAGA CACTTCAGCA GGAAAGACTG CGGCAGAGAG CTTGCTGGAC CCAGTGGAGT    60

ACTG                                                                 64
```

( 2 ) INFORMATION FOR SEQ ID NO:3:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
GAACAGGTAC GTAAAATTCA AGGCGATGGT GCGGCTCTGC AGGAAAAGCT GTGCGCAACC    60
```

( 2 ) INFORMATION FOR SEQ ID NO:4:

( i ) SEQUENCE CHARACTERISTICS:
  ( A ) LENGTH: 60 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:4:

TTTGTAGGTT GCGCACAGCT TTTCCTGCAG AGCCGCACCA TCGCCTTGAA TTTTACGTAC          60

( 2 ) INFORMATION FOR SEQ ID NO:5:

( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:5:

TACAAACTGT GCCACCCTGA GGAACTGGTG CTGCTCGGTC ACTCTCTG          48

( 2 ) INFORMATION FOR SEQ ID NO:6:

( i ) SEQUENCE CHARACTERISTICS:
    ( A ) LENGTH: 51 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:6:

CGGGATCCCC AGAGAGTGAC CGAGCAGCAC CAGTTCCTCA GGGTGGCACA G          51

( 2 ) INFORMATION FOR SEQ ID NO:7:

( i ) SEQUENCE CHARACTERISTICS:
    ( A ) LENGTH: 63 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:7:

GGGATCCCGT GGGCTCCACT GAGCTCTTGC CCGTCCCAAG CTTTACAACT GGCAGGCTGC          60

TTG          63

( 2 ) INFORMATION FOR SEQ ID NO:8:

( i ) SEQUENCE CHARACTERISTICS:
    ( A ) LENGTH: 60 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:8:

CTGGCTCAAG CAGCCTGCCA GTTGTAAAGC TTGGGACGGG CAAGAGCTCA GTGGAGCCCA          60

( 2 ) INFORMATION FOR SEQ ID NO:9:

( i ) SEQUENCE CHARACTERISTICS:
    ( A ) LENGTH: 63 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:9:

AGCCAGCTGC ACTCCGGTCT GTTCCTGTAC CAGGGTCTGC TGCAGGCTCT AGAAGGCATC          60

TCT          63

( 2 ) INFORMATION FOR SEQ ID NO:10:

(i) SEQUENCE CHARACTERISTICS:
    (A) LENGTH: 63 base pairs
    (B) TYPE: nucleic acid
    (C) STRANDEDNESS: single
    (D) TOPOLOGY: linear (xi) SEQUENCE DESCRIPTION: SEQ ID NO:10:

TTCAGGAGAG ATGCCTTCTA GAGCCTGCAG CAGACCCTGG TACAGGAACA GACCGGAGTG    60

CAG    63

(2) INFORMATION FOR SEQ ID NO:11:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:11:

CCTGAATTGG GGCCCACCCT GGACACACTG CAGCTGGACG TTGCCGACTT CGCTACTACC    60

(2) INFORMATION FOR SEQ ID NO:12:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (xi) SEQUENCE DESCRIPTION: SEQ ID NO:12:

TTGCCATATG GTAGTAGCGA AGTCGGCAAC GTCCAGCTGC AGTGTGTCCA GGGTGGGCCC    60

CAA    63

(2) INFORMATION FOR SEQ ID NO:13:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (xi) SEQUENCE DESCRIPTION: SEQ ID NO:13:

ATATGGCAAC AGATGGAGGA ACTGGGTATG GCTCCGGCAC TGCAGCCGAC TCAGGGTGCG    60

ATG    63

(2) INFORMATION FOR SEQ ID NO:14:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:14:

TGCTGGCATC GCACCCTGAG TCGGCTGCAG TGCCGGAGCC ATACCCAGTT CCTCCATCTG    60

(2) INFORMATION FOR SEQ ID NO:15:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:15:

CCAGCATTCG CCTCTGCTTT CCAGCGGCGC GCAGGCGGTG TTCTGGTTGC CTCCCATCTT    60

( 2 ) INFORMATION FOR SEQ ID NO:16:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

GCTCTGAAGA TGGGAGGCAA CCAGAACACC GCCTGCGCGC CGCTGGAAAG CAGAGGCGAA     60

( 2 ) INFORMATION FOR SEQ ID NO:17:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

CAGAGCTTCC TCGAGGTGTC TTACCGCGTT CTGCGTCACC TGGCCCAGCC GTTAG     55

( 2 ) INFORMATION FOR SEQ ID NO:18:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

TCGACTTACG GCTGGGCCAG GTGACGCAGA ACGCGGTAAG ACACCTCGAG GAA     53

( 2 ) INFORMATION FOR SEQ ID NO:19:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

TACAACTGGC AGGCTGCTTG A     21

( 2 ) INFORMATION FOR SEQ ID NO:20:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

GACGTTGCCG ACTTCGCTAC T     21

( 2 ) INFORMATION FOR SEQ ID NO:21:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

TGCCGGAGCC ATACCCAGTT C     21

( 2 ) INFORMATION FOR SEQ ID NO:22:

( i ) SEQUENCE CHARACTERISTICS:

( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

GCCTGCCAGT TGTAAAGCTT G                                                                    2 1

( 2 ) INFORMATION FOR SEQ ID NO:23:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

GCACCATCGC CTTGAATTTT ACGTAG                                                               2 6

( 2 ) INFORMATION FOR SEQ ID NO:24:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

AATTCAGTAC TCCACTGGGT CCAGCAAGCT CTCTGCCGCA GTCTTTCCTG CTGAAGTCTC          6 0

T C                                                                                        6 2

( 2 ) INFORMATION FOR SEQ ID NO:25:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

CTGTTCGAGA GACTTCAGCA GGAAAGACTG CGGCAGAGAG CTTGCTGGAC CCAGTGGAGT          6 0

ACTG                                                                                       6 4

( 2 ) INFORMATION FOR SEQ ID NO:26:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

GAACAGGTAC GTAAAATTCA AGGCAGCGGT GCGGCTCTGC AGGAAAAGCT GTGCGCAACC          6 0

( 2 ) INFORMATION FOR SEQ ID NO:27:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

TTTGTAGGTT GCGCACAGCT TTTCCTGCAG AGCCGCACCG CTGCCTTGAA TTTTACGTAC          6 0

( 2 ) INFORMATION FOR SEQ ID NO:28:

( i ) SEQUENCE CHARACTERISTICS:

(A) LENGTH: 29 base pairs
(B) TYPE: nucleic acid
(C) STRANDEDNESS: single
(D) TOPOLOGY: linear (xi) SEQUENCE DESCRIPTION: SEQ ID NO:28:

CTTCAGCAGG AAAGAACGCG GCAGAGAGC 29

(2) INFORMATION FOR SEQ ID NO:29:

(i) SEQUENCE CHARACTERISTICS:
(A) LENGTH: 33 base pairs
(B) TYPE: nucleic acid
(C) STRANDEDNESS: single
(D) TOPOLOGY: linear (xi) SEQUENCE DESCRIPTION: SEQ ID NO:29:

GCTTGGGAAG AGCAAGAGCT CAGAGAAGCC CAC 33

(2) INFORMATION FOR SEQ ID NO:30:

(i) SEQUENCE CHARACTERISTICS:
(A) LENGTH: 40 base pairs
(B) TYPE: nucleic acid
(C) STRANDEDNESS: single
(D) TOPOLOGY: linear (xi) SEQUENCE DESCRIPTION: SEQ ID NO:30:

CTGTTGCCAT ATGCTAGAAG CGAAGTCTTC AACGTCCAGC 40

(2) INFORMATION FOR SEQ ID NO:31:

(i) SEQUENCE CHARACTERISTICS:
(A) LENGTH: 27 base pairs
(B) TYPE: nucleic acid
(C) STRANDEDNESS: single
(D) TOPOLOGY: linear (xi) SEQUENCE DESCRIPTION: SEQ ID NO:31:

GCTCAGTGGA GCTTTCGGGA TCCCCAG 27

(2) INFORMATION FOR SEQ ID NO:32:

(i) SEQUENCE CHARACTERISTICS:
(A) LENGTH: 27 base pairs
(B) TYPE: nucleic acid
(C) STRANDEDNESS: single
(D) TOPOLOGY: linear (xi) SEQUENCE DESCRIPTION: SEQ ID NO:32:

ACGCAGAACG CGGCGAGACA CCTCGAG 27

(2) INFORMATION FOR SEQ ID NO:33:

(i) SEQUENCE CHARACTERISTICS:
(A) LENGTH: 29 base pairs
(B) TYPE: nucleic acid
(C) STRANDEDNESS: single
(D) TOPOLOGY: linear (xi) SEQUENCE DESCRIPTION: SEQ ID NO:33:

GTTCGAGAGA CTTTTCCAGG AAAGACTGC 29

(2) INFORMATION FOR SEQ ID NO:34:

(i) SEQUENCE CHARACTERISTICS:
(A) LENGTH: 33 base pairs
(B) TYPE: nucleic acid
(C) STRANDEDNESS: single
(D) TOPOLOGY: linear ( x i ) SEQUENCE DESCRIPTION: SEQ ID NO:34:

CCTGCAGTTT CGCAGCGCTA GCTTGAATTT TAC        33

( 2 ) INFORMATION FOR SEQ ID NO:35:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:35:

CAGAGAGTGA GCGAGCTTCA CCAGTTCCTC AGCGTGG        37

( 2 ) INFORMATION FOR SEQ ID NO:36:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:36:

GCTCAGTGGA GCTTTCGGGA TAGCCAGAG        29

( 2 ) INFORMATION FOR SEQ ID NO:37:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:37:

CAGCTTTTCC TGCAGACGCG CAGCGCTAGC        30

( 2 ) INFORMATION FOR SEQ ID NO:38:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:38:

CCGCTGCCTT GAATACGACG TACCTGTTC        29

( 2 ) INFORMATION FOR SEQ ID NO:39:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:39:

GGTTGCGCAC AGACGTTCCT GCAGAGCCGC        30

( 2 ) INFORMATION FOR SEQ ID NO:40:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:40:

GGTGGCACAG ACGGTAGGTT GCGCACAGC        29

( 2 ) INFORMATION FOR SEQ ID NO:41:

( i ) SEQUENCE CHARACTERISTICS:
　　　　( A ) LENGTH: 45 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:41:

CGCGGCAGAG AGCTTGCACG GTAGGTTGGA GCCATTGTCG ATACC　　　　　　　　　　45

( 2 ) INFORMATION FOR SEQ ID NO:42:

( i ) SEQUENCE CHARACTERISTICS:
　　　　( A ) LENGTH: 24 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:42:

GCAAGAGCTC AGAGAAGCCC ACGG　　　　　　　　　　　　　　　　　　　　24

( 2 ) INFORMATION FOR SEQ ID NO:43:

( i ) SEQUENCE CHARACTERISTICS:
　　　　( A ) LENGTH: 39 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:43:

CAGCCTGCCA GTTGTAAAGC TTGGGAGCTG CAAGAGCTC　　　　　　　　　　　　39

( 2 ) INFORMATION FOR SEQ ID NO:44:

( i ) SEQUENCE CHARACTERISTICS:
　　　　( A ) LENGTH: 27 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:44:

GCTCAGAGAA GCTTTCGGGA TCCCCAG　　　　　　　　　　　　　　　　　　27

( 2 ) INFORMATION FOR SEQ ID NO:45:

( i ) SEQUENCE CHARACTERISTICS:
　　　　( A ) LENGTH: 46 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:45:

CGGGATAGCC AGAGAGTGAG CGAGTTTCAC CAGTTCCTCA GCGTGG　　　　　　　　46

( 2 ) INFORMATION FOR SEQ ID NO:46:

( i ) SEQUENCE CHARACTERISTICS:
　　　　( A ) LENGTH: 174 amino acids
　　　　( B ) TYPE: amino acid
　　　　( D ) TOPOLOGY: linear ( i x ) FEATURE:
　　　　( A ) NAME/KEY:
　　　　( B ) LOCATION: 36
　　　　( D ) OTHER INFORMATION: /note="Xaa is either Cys or is
　　　　　　　Val Ser Glu Cys"

( x i ) SEQUENCE DESCRIPTION: SEQ ID NO:46:

```
    Thr Pro Leu Gly Pro Ala Ser Ser Leu Pro Gln Ser Phe Leu Leu Lys
    1               5                   10                  15

Cys Leu Glu Gln Val Arg Lys Ile Gln Gly Asp Gly Ala Ala Leu Gln
                20                  25                  30

Glu Lys Leu Xaa Ala Thr Tyr Lys Leu Cys His Pro Glu Glu Leu Val
            35                  40                  45

Leu Leu Gly His Ser Leu Gly Ile Pro Trp Ala Pro Leu Ser Ser Cys
        50                  55                  60

Pro Ser Gln Ala Leu Gln Leu Ala Gly Cys Leu Ser Gln Leu His Ser
    65                  70                  75                  80

Gly Leu Phe Leu Tyr Gln Gly Leu Leu Gln Ala Leu Glu Gly Ile Ser
                    85                  90                  95

Pro Glu Leu Gly Pro Thr Leu Asp Thr Leu Gln Leu Asp Val Ala Asp
                100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
        130                 135                 140

Gln Arg Arg Ala Gly Gly Val Leu Val Ala Ser His Leu Gln Ser Phe
    145                 150                 155                 160

Leu Glu Val Ser Tyr Arg Val Leu Arg His Leu Ala Gln Pro
                    165                 170
```

( 2 ) INFORMATION FOR SEQ ID NO:47:

( i ) SEQUENCE CHARACTERISTICS:
        ( A ) LENGTH: 168 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:47:

```
AATTCTGGCA AATATTCTGA AATGAGCTGT TGACAATTAA TCATCGAACT AGTTAACTAG      60

TACGCAAGTT CACGTAAAAA GGGTATCGAC AATGGTACCC GGGGATCCTC TAGAGTCGAC     120

CTGCAGGCAT GCAAGCTTAG CCCGCCTAAT GAGCGGGCTT TTTTTTAT                  168
```

( 2 ) INFORMATION FOR SEQ ID NO:48:

( i ) SEQUENCE CHARACTERISTICS:
        ( A ) LENGTH: 534 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 9..530

( x i ) SEQUENCE DESCRIPTION: SEQ ID NO:48:

```
AATTCAGT ACT CCA CTG GGT CCA GCA AGC TCT CTG CCG CAG TCT TTC CTG       50
         Thr Pro Leu Gly Pro Ala Ser Ser Leu Pro Gln Ser Phe Leu
         1               5                   10

CTG AAG TGT CTC GAA CAG GTA CGT AAA ATT CAA GGC GAT GGT GCG GCT        98
Leu Lys Cys Leu Glu Gln Val Arg Lys Ile Gln Gly Asp Gly Ala Ala
15                  20                  25                  30

CTG CAG GAA AAG CTG TGC GCA ACC TAC AAA CTG TGC CAC CCT GAG GAA       146
Leu Gln Glu Lys Leu Cys Ala Thr Tyr Lys Leu Cys His Pro Glu Glu
                35                  40                  45

CTG GTG CTG CTC GGT CAC TCT CTG GGG ATC CCG TGG GCT CCA CTG AGC       194
Leu Val Leu Leu Gly His Ser Leu Gly Ile Pro Trp Ala Pro Leu Ser
            50                  55                  60

TCT TGC CCG TCC CAA GCT TTA CAA CTG GCA GGC TGC TTG AGC CAG CTG       242
```

```
Ser Cys Pro Ser Gln Ala Leu Gln Leu Ala Gly Cys Leu Ser Gln Leu
    65                  70                  75

CAC TCC GGT CTG TTC CTG TAC CAG GGT CTG CTG CAG GCT CTA GAA GGC         290
His Ser Gly Leu Phe Leu Tyr Gln Gly Leu Leu Gln Ala Leu Glu Gly
    80                  85                  90

ATC TCT CCT GAA TTG GGG CCC ACC CTG GAC ACA CTG CAG CTG GAC GTT         338
Ile Ser Pro Glu Leu Gly Pro Thr Leu Asp Thr Leu Gln Leu Asp Val
95                  100                 105                 110

GCC GAC TTC GCT ACT ACC ATA TGG CAA CAG ATG GAG GAA CTG GGT ATG         386
Ala Asp Phe Ala Thr Thr Ile Trp Gln Gln Met Glu Glu Leu Gly Met
                115                 120                 125

GCT CCG GCA CTG CAG CCG ACT CAG GGT GCG ATG CCA GCA TTC GCC TCT         434
Ala Pro Ala Leu Gln Pro Thr Gln Gly Ala Met Pro Ala Phe Ala Ser
            130                 135                 140

GCT TTC CAG CGG CGC GCA GGC GGT GTT CTG GTT GCC TCC CAT CTT CAG         482
Ala Phe Gln Arg Arg Ala Gly Gly Val Leu Val Ala Ser His Leu Gln
        145                 150                 155

AGC TTC CTC GAG GTG TCT TAC CGC GTT CTG CGT CAC CTG GCC CAG CCG         530
Ser Phe Leu Glu Val Ser Tyr Arg Val Leu Arg His Leu Ala Gln Pro
    160                 165                 170

TAAG                                                                     534
```

( 2 ) INFORMATION FOR SEQ ID NO:49:

( i ) SEQUENCE CHARACTERISTICS:
        ( A ) LENGTH: 534 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 9..530

( x i ) SEQUENCE DESCRIPTION: SEQ ID NO:49:

```
AATTCAGT ACT CCA CTG GGT CCA GCA AGC TCT CTG CCG CAG TCT TTC CTG        50
         Thr Pro Leu Gly Pro Ala Ser Ser Leu Pro Gln Ser Phe Leu
          1               5                   10

CTG AAG TCT CTC GAA CAG GTA CGT AAA ATT CAA GGC AGC GGT GCG GCT         98
Leu Lys Ser Leu Glu Gln Val Arg Lys Ile Gln Gly Ser Gly Ala Ala
15                  20                  25                  30

CTG CAG GAA AAG CTG TGC GCA ACC TAC AAA CTG TGC CAC CCT GAG GAA         146
Leu Gln Glu Lys Leu Cys Ala Thr Tyr Lys Leu Cys His Pro Glu Glu
                35                  40                  45

CTG GTG CTG CTC GGT CAC TCT CTG GGG ATC CCG TGG GCT CCA CTG AGC         194
Leu Val Leu Leu Gly His Ser Leu Gly Ile Pro Trp Ala Pro Leu Ser
            50                  55                  60

TCT TGC CCG TCC CAA GCT TTA CAA CTG GCA GGC TGC TTG AGC CAG CTG         242
Ser Cys Pro Ser Gln Ala Leu Gln Leu Ala Gly Cys Leu Ser Gln Leu
        65                  70                  75

CAC TCC GGT CTG TTC CTG TAC CAG GGT CTG CTG CAG GCT CTA GAA GGC         290
His Ser Gly Leu Phe Leu Tyr Gln Gly Leu Leu Gln Ala Leu Glu Gly
    80                  85                  90

ATC TCT CCT GAA TTG GGG CCC ACC CTG GAC ACA CTG CAG CTG GAC GTT         338
Ile Ser Pro Glu Leu Gly Pro Thr Leu Asp Thr Leu Gln Leu Asp Val
95                  100                 105                 110

GCC GAC TTC GCT ACT ACC ATA TGG CAA CAG ATG GAG GAA CTG GGT ATG         386
Ala Asp Phe Ala Thr Thr Ile Trp Gln Gln Met Glu Glu Leu Gly Met
                115                 120                 125

GCT CCG GCA CTG CAG CCG ACT CAG GGT GCG ATG CCA GCA TTC GCC TCT         434
Ala Pro Ala Leu Gln Pro Thr Gln Gly Ala Met Pro Ala Phe Ala Ser
            130                 135                 140

GCT TTC CAG CGG CGC GCA GGC GGT GTT CTG GTT GCC TCC CAT CTT CAG         482
Ala Phe Gln Arg Arg Ala Gly Gly Val Leu Val Ala Ser His Leu Gln
```

|     | 145 |     |     |     | 150 |     |     |     |     | 155 |     |     |     |     |     |
|-----|-----|-----|-----|-----|-----|-----|-----|-----|-----|-----|-----|-----|-----|-----|-----|
| AGC | TTC | CTC | GAG | GTG | TCT | TAC | CGC | GTT | CTG | CGT | CAC | CTG | GCC | CAG | CCG | 530 |
| Ser | Phe | Leu | Glu | Val | Ser | Tyr | Arg | Val | Leu | Arg | His | Leu | Ala | Gln | Pro |
|     | 160 |     |     |     |     | 165 |     |     |     | 170 |     |     |     |     |     |

TAAG     534

( 2 ) INFORMATION FOR SEQ ID NO:50:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:50:

GAATTCAACA AAACGGTTGA CAACATGAAG TAAACACGGT ACGATGTACC ACAAGTTCAC     60

GTAAAAGGG TATCGACAAT G     81

( 2 ) INFORMATION FOR SEQ ID NO:51:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:51:

TCGACATTAT ATTACTAATT AATTGGGGAC CCTAGAGGTC CCCTTTTTA TTTTAAAAG     60

CATGCGA     67

( 2 ) INFORMATION FOR SEQ ID NO:52:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:52:

TCGACATTAT ATTACTAATT AATTGGGGAC CCTAGAGGTC CCCTTTTTA TTTTAAAAGC     60

ATGCGGATCC C     71

( 2 ) INFORMATION FOR SEQ ID NO:53:

( i ) SEQUENCE CHARACTERISTICS:
        ( A ) LENGTH: 118 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

AATTCTGGCA ATATTCTGA ATGAGCTGT TGACAATTAA TCATCGAACT AGTTAACTAG     60

TACGCAGAGC TCAATCTAGA GGGTATTAAT AATGTTCCCA TTGGAGGATG ATTAAATG     118

( 2 ) INFORMATION FOR SEQ ID NO:54:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:54:

AGCTCCATAT GGTACCAGAT CTCTCGAGAG TACTT     35

( 2 ) INFORMATION FOR SEQ ID NO:55:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:55:

```
AGCTCAGCTG CAGCATATGG TAC                                                23
```

( 2 ) INFORMATION FOR SEQ ID NO:56:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:56:

```
TCGACATTAT ATTACTAATT AATTGGGGAC CCTAGAGGTC CCCTTTTTA TTTTAAAAAG          60
CATGCGGATC CC                                                            72
```

( 2 ) INFORMATION FOR SEQ ID NO:57:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:57:

```
AATTCAACAA AACGGTTGAC AACATGAAGT AAACACGGTA CGATGTACCA CAAGTTCACG         60
TAAAAGGGT ATCGACAATG GTAC                                                84
```

( 2 ) INFORMATION FOR SEQ ID NO:58:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:58:

```
CATTGTCGAT ACCCTTTTTA CGTGAACTTG TGGTACATCG TACCGTGTTT ACTTCATGTT         60
GTCAACCGTT TTGTTG                                                        76
```

( 2 ) INFORMATION FOR SEQ ID NO:59:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:59:

```
AATTCGCATG CGGATCCATC GATC                                               24
```

( 2 ) INFORMATION FOR SEQ ID NO:60:

( i ) SEQUENCE CHARACTERISTICS:
        ( A ) LENGTH: 166 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:60:

```
CGATAAAAAA AAGCCCGCTC ATTAGGCGGG CTAAGCTTGC ATGCCTGCAG GTCGACTCTA         60
```

GAGGATCCCC GGGTACCATT GTCGATACCC TTTTTACGTG AACTTGCGTA CTAGTTAACT    120

AGTTCGATGA TTAATTGTCA ACAGCTCATT TCAGAATATT TGCCAG    166

( 2 ) INFORMATION FOR SEQ ID NO:61:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:61:

AGCTTCGCAT GCTTTTTAAA ATAAAAAGG GGACCTCTAG GGTCCCCAAT TAATTAGTAA    60

TATAATG    67

( 2 ) INFORMATION FOR SEQ ID NO:62:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:62:

CAAGGGGATC CGCATGCTTT TAAAATAAAA AAGGGGACCT CTAGGGTCCC CAATTAATTA    60

GTAATATAAT G    71

( 2 ) INFORMATION FOR SEQ ID NO:63:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:63:

CTAGAAGTAC TCTCGAGAGA TCTGGTACCA TATGG    35

( 2 ) INFORMATION FOR SEQ ID NO:64:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:64:

CATATGCTGC AGCTG    15

( 2 ) INFORMATION FOR SEQ ID NO:65:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:65:

CAAGGGGATC CGCATGCTTT TTAAAATAAA AAAGGGGACC TCTAGGGTCC CCAATTAATT    60

AGTAATATAA TG    72

( 2 ) INFORMATION FOR SEQ ID NO:66:

( i ) SEQUENCE CHARACTERISTICS:
        ( A ) LENGTH: 24 base pairs
        ( B ) TYPE: nucleic acid (C) STRANDEDNESS: single
(D) TOPOLOGY: linear (xi) SEQUENCE DESCRIPTION: SEQ ID NO:66:

CCGAGATCGA TGGATCCGCA TGCG      24